(12) United States Patent
Lingor et al.

(10) Patent No.: US 9,980,972 B2
(45) Date of Patent: May 29, 2018

(54) RHO KINASE INHIBITORS FOR USE IN TREATING FAMILIAL AMYOTROPHIC LATERAL SCLEROSIS

(71) Applicant: GEORG-AUGUST-UNIVERSITÄT GÖTTINGEN STIFTUNG ÖFFENTLICHEN RECHTS, UNIVERSITÄTSMEDIZIN, Göttingen (DE)

(72) Inventors: Paul Lingor, Göttingen (DE); Lars Tönges, Göttingen (DE)

(73) Assignee: GEORG-AUGUST-UNIVERSITÄT GÖTTINGEN STIFTUNG ÖFFENTLICHEN RECHTS, UNIVERSITÄTSMEDIZIN, Göttingen (DE)

( * ) Notice: Subject to any disclaimer, the term of this patent is extended or adjusted under 35 U.S.C. 154(b) by 537 days.

(21) Appl. No.: 14/384,549

(22) PCT Filed: Mar. 11, 2013

(86) PCT No.: PCT/EP2013/054804
§ 371 (c)(1),
(2) Date: Sep. 11, 2014

(87) PCT Pub. No.: WO2013/135596
PCT Pub. Date: Sep. 19, 2013

(65) Prior Publication Data
US 2015/0031683 A1 Jan. 29, 2015

Related U.S. Application Data

(60) Provisional application No. 61/609,576, filed on Mar. 12, 2012.

(51) Int. Cl.
*A61K 31/55* (2006.01)
*A61K 31/47* (2006.01)
*A61K 31/551* (2006.01)

(52) U.S. Cl.
CPC ............ *A61K 31/551* (2013.01); *A61K 31/47* (2013.01); *A61K 31/55* (2013.01)

(58) Field of Classification Search
CPC ................................ A61K 31/47; A61K 31/55
USPC .................................................. 514/218, 307
See application file for complete search history.

(56) References Cited

U.S. PATENT DOCUMENTS

| 4,678,783 | A | 7/1987 | Hidaka et al. |
| 5,942,505 | A | 8/1999 | Kawakubo et al. |
| 2005/0096253 | A1 | 5/2005 | Monnier et al. |
| 2012/0010196 | A1* | 1/2012 | Qin .................... A61K 31/4409 514/218 |

FOREIGN PATENT DOCUMENTS

| CA | 2466424 A1 * | 5/2003 | ............. A61K 31/00 |
| EP | 1 110 553 A1 | 6/2001 | |
| JP | 2007-246466 A | 9/2007 | |
| JP | 2009-292782 A | 12/2009 | |
| WO | WO 2005/117896 A1 | 12/2005 | |
| WO | WO 2009/155777 A1 | 12/2009 | |
| WO | WO 2009155777 A1 * | 12/2009 | ........... A61K 9/0019 |

OTHER PUBLICATIONS

WO 2009/155777 A1 (2009), English Translation.*
Baba, Hironori et al., "Protective effects of cold spinoplegia with fasudil against ischemic spinal cord injury in rabbits", J. of Vascular Surgery, vol. 51, No. 2, Feb. 2010, pp. 445-452, XP26876516.
Bermel, C. et al., "Combined inhibition of Cdk5 and ROCK additively increase cell survival, but not the regenerative response in regenerating retinal ganglion cells." Mol Cell Neuroscience, vol. 42, No. 4, 2009, pp. 427-437.
Bowerman M. et al., "Fasudil improves survival and promotes skeletal muscle development in a mouse model of spinal muscular atrophy", BMC Medicine, vol. 10, No. 24, Mar. 7, 2012.
Bowerman, M. et al., "Rho-kinase inactivation prolongs survival of an intermediate SMA mouse model", Human Molecular Genetics, 2010, vol. 19, No. 8, pp. 1468-1478.
Cedarbaum, J. et al., The ALSFRS-R: a revised ALS functional rating scale that incorporates assessments of respiratory function. J. of the Neurological Sciences, vol. 169, 1999, pp. 13-21.
Cuny, G. D., "Kinase inhibitors as potential therapeutics for acute and chronic neurodegenerative conditions", Current Pharmaceutical Design, vol. 15, 2009, pp. 3919-3939.
Davies, S. P. et al., "Specificity and mechanism of action of some commonly used protein kinase inhibitors", Biochem J., No. 351, 2000, pp. 95-105.
de Carvalho M. and Swash, M., "Amyotrophic lateral sclerosis: an update", Current Opinion in Neurology, vol. 24, 2011, pp. 497-503.
de Carvalho M. et al., "Electrodiagnostic criteria for diagnosis of ALS", Clinical Neurophysiology, vol. 119, 2008, pp. 497-503.
Graeber, M., "Changing Face of Microglia", Science, vol. 330, 2010, pp. 783-788.
Gurney, M. et al., "Motor Neuron Degeneration in mice that express a human Cu,Zn superoxide Dismutase Mutation", Science, vol. 264, Jun. 17, 1994, pp. 1772-1775.
Henkel, J. et al., "Microglia in ALS: The Good, The Bad, and the Resting", J. of Neuroimmune Pharmacology, vol. 4, 2009, pp. 389-398.
Kong, J. et al., "Massive mitochondrial degeneration in motor neurons triggers the onset of amyotrophic lateral sclerosis in mice expressing a mutant SOD1", J. of Neuroscience, vol. 18, No. 9, May 1, 1998, pp. 3241-3250.
Li, M. et al., "Y-27632 Improves rotarod performance and reduces huntingtin levels in R6/2 mice", Neurobiology of Disease, vol. 36, 2009, pp. 413-420.
Lingor, P. et al., "Axonal degeneration as a therapeutic target in the CNS", Cell and Tissue Research, vol. 349, No. 1, Mar. 6, 2012, pp. 289-311.

(Continued)

*Primary Examiner* — Kevin E Weddington
(74) *Attorney, Agent, or Firm* — Birch, Stewart, Kolasch & Birch, LLP

(57) ABSTRACT

The invention relates to a new use of a known Rho kinase inhibitor, fasudil or a fasudil derivative selected from hydroy-fasudil or dimethylfasudil, in the treatment of amyotrophic lateral sclerosis (ALS).

16 Claims, 22 Drawing Sheets

(56) References Cited

OTHER PUBLICATIONS

Lingor, P. et al., "Inhibition of Rho kinase (ROCK) increases neurite outgrowth on chondroitin sulphate proteoglycan in vitro and axonal regenration in the adult optic nerve in vivo", J. of Neurochemistry, vol. 103, 2007, pp. 181-189.
Lingor, P. et al., "ROCK inhibition and CNTF interact on intrinsic signaling pathways and differentially regulate survival and regeneration in retinal ganglion cells", Brain, vol. 131, 2008, pp. 250-263.
Meyer, G. et al., "Antiprogesterone therapy uncouples axonal loss from demyelination in a transgenic rat model of CMT1A neuropathy", Ann Neurol, vol. 61, 2007, pp. 61-72.
Pitzer, C. et al., "Granulocyte-colony stimulating factor improves outcome in a mouse model of amyotrophic lateral sclerosis", Brain, vol. 131, 2008, pp. 3335-3347.
Planchamp, V. et al., "BAGI promotes axonal outgrowth and regeneration in vivo via Raf-1 and reduction of ROCK activity", Brain, vol. 131, 2008, pp. 2606-2619.
Regen, T. et al., "CD14 and TRIF govern distinct responsiveness and responses in mouse microglial TLR4 challenges by structural variants of LPS", Brain, Behavior, and Immunity, vol. 25, 2011, pp. 957-970.
Tonges, L. et al., "Inhibition of rho kinase enhances survival of dopaminergic neurons and attenuates axonal loss in a mouse model of Parkinson's disease", Brain, vol. 135, Oct. 19, 2012, pp. 3355-3370.

\* cited by examiner

MN survival cultured with astrocyte conditioned medium after KA 125μM for 24h on DIV7

C end-stage

SOD1$^{G93A}$ Veh    SOD1$^{G93A}$ Fas30    SOD1$^{G93A}$ Fas100

D d100

WT Veh    SOD1$^{G93A}$ Veh    SOD1$^{G93A}$ Fas30

RHO KINASE INHIBITORS FOR USE IN TREATING FAMILIAL AMYOTROPHIC LATERAL SCLEROSIS

CROSS REFERENCE TO RELATED APPLICATIONS

This application is the National Phase of PCT International Application No. PCT/EP2013/054804, filed on Mar. 11, 2013, which claims priority under 35 U.S.C. 119(e) to U.S. Provisional Application No. 61/609,576, filed on Mar. 12, 2012, all of which are hereby expressly incorporated by reference into the present application.

The present invention relates to a new use of a known Rho kinase inhibitor in the treatment of amyotrophic lateral sclerosis (ALS).

BACKGROUND OF THE INVENTION

Amyotrophic lateral sclerosis (ALS), also known as Lou Gehrig's disease, is one of the most common neuromuscular diseases worldwide, and people of all races and ethnic backgrounds are affected. ALS is most commonly diagnosed in people between 40 and 60 years of age, and men are affected slightly more often than women. One or two out of 100,000 people develop ALS each year and estimated 5,000 people in the United States are diagnosed with the disease each year. ALS is a progressive disease characterized by rapidly progressive weakness, muscle atrophy and fasciculation, spasticity, dysarthria, dysphagia, and respiratory compromise. It is a neurodegenerative movement disorder caused by the degeneration of neurons located in the ventral horn of the spinal cord and the cortical neurons. Unable to function, the muscles weaken and atrophy. Cognitive function is generally spared for most patients although ~5% also develop frontotemporal dementia. ~30-50% of patients also show subtle cognitive changes which can be revealed by detailed neuropsychological testing.

There is a known hereditary factor in familial ALS, although this accounts for only around 5-10% of all cases. Approximately 20% of familial cases of ALS have been linked with an autosomal dominant genetic defect on chromosome 21, coding for superoxide dismutase (SOD1). The most common ALS causing SOD1 mutation in North America is A4V, characterized by an exceptionally rapid progression from onset to death. A recent study identified a gene called FUS ("Fused in Sarcoma", ALS6) as being responsible for 1 in 20 cases of familial ALS.

The degeneration of the first and second motoneuron in ALS is a multifactorial pathologic process. A variety of neuroprotective agents have been examined to counteract initiation and/or progression of disease, but only the glutamate antagonist Riluzole (marketed by Sanofi-Aventis under the trademark Rilutek), which targets glutamate transporters, has reached clinical use so far. It has been found to improve survival to a modest extent and also extends the time before a person needs ventilation support. Riluzole does not reverse the damage already done to motor neurons, and people taking it must be monitored for liver damage (occurring in ~10% of people taking the drug). Further known side-effects or Riluzole are nausea and fatigue which may cause patients to discontinue treatment.

Fasudil is a potent Rho-kinase (ROCK) inhibitor and vasodilator. In the past, it has been used for the treatment of cerebral vasospasm, which is often due to subarachnoid hemorrhage, as well as to improve the cognitive decline seen in stroke victims. Moreover, it has been found to be useful for the treatment of pulmonary hypertension and to enhance memory and improve the prognosis of Alzheimer patients.

The inventors have previously shown that pharmacological inhibition of rho kinase by Y-27632 (a 4-aminopyridine derivative) and Fasudil (an isoquinoline derivative) does not only enhance regeneration, but also survival of lesioned CNS neurons in vivo and in vitro (Lingor, Teusch et al. 2007; Lingor, Tonges et al. 2008; Planchamp, Bermel et al. 2008; Bermel, Tonges et al. 2009). In addition to the established effects on the actin cytoskeleton, the inventors could show that inhibition of ROCK results in activation of intracellular pathways mediating neuronal survival. Further, the inventors have demonstrated that pharmacologic ROCK inhibition in the optic nerve lesion paradigm leads to a regeneration of lesion optic nerve axons and is able to improve survival of lesioned retinal ganglion cells (Lingor et al. 2010). The neuroprotective potential of ROCK inhibition in neurodegenerative disease has been further corroborated by other groups. For example, an improvement of neurological function and an increase of survival in animal models of Huntington's disease and SMA was reported (Li, Huang et al. 2009; Bowerman, Beauvais et al. 2010). However, a distinct survival prolonging effect in these animals models was only shown in rather acute neurodegenerative models like in the optic nerve lesion paradigm where retinal ganglion cell survival is evaluated 14 days after lesion and in the SMA model in which mice usually die after several weeks of life.

WO 2009/155777 A1 relates to the application of Fasudil in inducing regeneration of stem cells of adult cranial nerves. WO 2005/117896 A1 discloses pharmaceutical formulations of Fasudil and their use in the treatment of inter alia neuronal regeneration.

There is still a need in the art for new and effective treatments of ALS, in particular for treatments having less side-effects than the currently known ones.

SUMMARY OF THE INVENTION

The inventors decided to evaluate the therapeutic potential of the ROCK inhibitor Fasudil in the chronic SOD1 G93A mouse model of ALS ((B6SJL-TgN (SOD1-G93A) 1 Gur), that reflects the evolution of ALS disease clinically very well over a period of up to 22 weeks. The study was designed to comprise a presymptomatic (d50) and a symptomatic (d80) pharmacologic treatment group with Fasudil versus vehicle control. Parameters to be evaluated were disease onset, prolongation of survival and motor function. Furthermore, the inventors performed a detailed analysis of the influence of the treatment on ALS pathology in the central and peripheral nervous system thus taking into account all principally affected compartments of this neurodegenerative disease. In particular, the inventors undertook an extensive immunohistologic examination of the different treatment groups and evaluated as well survival of spinal cord motoneurons as glial infiltration with astrocytes and activated microglia in the spinal cord.

The data shown in the Examples demonstrates that treatment with Fas30 significantly prolongs survival of female SOD1 G93A mice. This beneficial effect is also reflected in an improved motor coordination function as demonstrated in the rotarod test and is mirrored immunopathologically in an increased survival of spinal cord motoneurons and a decreased astrogliotic infiltration of the spinal cord.

Accordingly, in a first aspect, the invention relates to a pharmaceutical composition, comprising 1-(5-isoquinolinesulfonyl)homopiperazine (fasudil), or a pharmaceutically acceptable salt thereof, for use in the treatment of a subject suffering from ALS. Preferably, the pharmaceutical composition consists of fasudil. In one embodiment, the ALS is sporadic ALS. In another embodiment, the ALS is familial ALS.

Likewise, the invention relates to a pharmaceutical composition, comprising 1-(5-isoquinolinesulfonyl)homopiperazine (fasudil), or a pharmaceutically acceptable salt thereof, for use in the treatment of a subject prone to suffer from ALS. Preferably, the pharmaceutical composition consists of fasudil. In one embodiment, the ALS is sporadic ALS. In a more preferred embodiment, the ALS is familial ALS.

The invention further relates to a pharmaceutical composition, comprising a fasudil derivative, or a pharmaceutically acceptable salt thereof, for use in the treatment of a subject suffering from ALS. Preferably, the pharmaceutical composition consists of said fasudil derivative. In one embodiment, the ALS is sporadic ALS. In another embodiment, the ALS is familial ALS. In one embodiment, the fasudil derivative is 1-(6-hydroxyl-5-isoquinolinesulfonyl)homopiperazine (hydroxyl-fasudil). In another embodiment, the fasudil derivative is (S)-(+)-2-Methyl-1-[(4-methyl-5-isoquinolinyl)sulfonyl]-hexahydro-1H-1,4-diazepine (dimethyl-fasudil).

Likewise, the inventions relates to a pharmaceutical composition, comprising a fasudil derivative, or a pharmaceutically acceptable salt thereof, for use in the treatment of a subject prone to suffer from ALS. Preferably, the pharmaceutical composition consists of said fasudil derivative. In one embodiment, the ALS is sporadic ALS. In a more preferred embodiment, the ALS is familial ALS. In one embodiment, the fasudil derivative is 1-(6-hydroxyl-5-isoquinolinesulfonyl)homopiperazine (hydroxyl-fasudil). In another embodiment, the fasudil derivative is (S)-(+)-2-Methyl-1-[(4-methyl-5-isoquinolinyl)sulfonyl]-hexahydro-1H-1,4-diazepine (dimethyl-fasudil).

Thus, the invention relates to a pharmaceutical composition, comprising or consisting of fasudil, or a fasudil derivative selected from hydroxyl-fasudil and dimethyl-fasudil, or a pharmaceutically acceptable salt thereof, for use in the treatment of a subject suffering or prone to suffer from sporadic or familial ALS.

In other words, a method of treating a subject suffering or prone to suffer from sporadic or familial ALS is provided, wherein the method comprises administering a pharmaceutical composition, comprising or consisting of fasudil, or a fasudil derivative selected from hydroxy-fasudil and dimethyl-fasudil, or a pharmaceutically acceptable salt thereof, to the subject.

In another aspect, the invention provides a pharmaceutical composition, comprising fasudil, or a pharmaceutically acceptable salt thereof, for use of improving motor coordination in a subject suffering from ALS. Preferably, the pharmaceutical composition consists of fasudil. In one embodiment, the ALS is sporadic ALS. In another embodiment, the ALS is familial ALS.

Likewise, the invention relates to a pharmaceutical composition, comprising fasudil, or a pharmaceutically acceptable salt thereof, for use of improving motor coordination in a subject prone to suffer from ALS. Preferably, the pharmaceutical composition consists of fasudil. In one embodiment, the ALS is sporadic ALS. In a more preferred embodiment, the ALS is familial ALS.

The invention further provides a pharmaceutical composition, comprising a fasudil derivative, or a pharmaceutically acceptable salt thereof, for use of improving motor coordination in a subject suffering from ALS. Preferably, the pharmaceutical composition consists of said fasudil derivative. In one embodiment, the ALS is sporadic ALS. In another embodiment, the ALS is familial ALS. In one embodiment, the fasudil derivative is 1-(6-hydroxyl-5-isoquinolinesulfonyl)homopiperazine (hydroxyl-fasudil). In another embodiment, the fasudil derivative is (S)-(+)-2-Methyl-1-[(4-methyl-5-isoquinolinyl)sulfonyl]-hexahydro-1H-1,4-diazepine (dimethyl-fasudil).

Likewise, the invention relates to a pharmaceutical composition, comprising a fasudil derivative, or a pharmaceutically acceptable salt thereof, for use of improving motor coordination in a subject prone to suffer from ALS. Preferably, the pharmaceutical composition consists of said fasudil derivative. In one embodiment, the ALS is sporadic ALS. In a more preferred embodiment, the ALS is familial ALS. In one embodiment, the fasudil derivative is 1-(6-hydroxyl-5-isoquinolinesulfonyl)homopiperazine (hydroxyl-fasudil). In another embodiment, the fasudil derivative is (S)-(+)-2-Methyl-1-[(4-methyl-5-isoquinolinyl)sulfonyl]-hexahydro-1H-1,4-diazepine (dimethyl-fasudil).

Thus, the invention relates to a pharmaceutical composition, comprising or consisting of 1-(5-isoquinolinesulfonyl)homopiperazine (fasudil), or a fasudil derivative selected from 1-(6-hydroxyl-5-isoquinolinesulfonyl)homopiperazine (hydroxyl-fasudil) and (S)-(+)-2-Methyl-1-[(4-methyl-5-isoquinolinyl)sulfonyl]-hexahydro-1H-1,4-diazepine (dimethyl-fasudil), or a pharmaceutically acceptable salt thereof, for use of improving motor coordination in a subject suffering or prone to suffer from sporadic or familial ALS.

In other words, the invention provides a method of improving motor coordination in a subject suffering or prone to suffer from sporadic or familial ALS, wherein the method comprises administering a pharmaceutical composition, comprising or consisting of fasudil, or a fasudil derivative selected from hydroxy-fasudil and dimethyl-fasudil, or a pharmaceutically acceptable salt thereof, to the subject. For example, an improvement of the motor coordination in a subject can be determined in accordance with the ALS functional rating scale.

Finally, the invention provides a method of prolonging lifetime of a subject suffering from ALS, wherein the method comprises administering a pharmaceutical composition, comprising fasudil, or a pharmaceutically acceptable salt thereof, to the subject. In one embodiment, the pharmaceutical composition consists of fasudil. The ALS may be sporadic ALS. Alternatively, the ALS may be familial ALS. Likewise, the invention provides a method of prolonging lifetime of a subject suffering from ALS, wherein the method comprises administering a pharmaceutical composition, comprising a fasudil derivative, or a pharmaceutically acceptable salt thereof, to the subject. In one embodiment, the pharmaceutical composition consists of said fasudil derivative. In one embodiment, the fasudil derivative is hydroxyl-fasudil. In another embodiment, the fasudil derivative is dimethyl-fasudil. The ALS may be sporadic ALS. Alternatively, the ALS may be familial ALS.

Also provided is a method of prolonging lifetime of a subject prone to suffer from ALS, wherein the method comprises administering a pharmaceutical composition, comprising fasudil, or a pharmaceutically acceptable salt thereof, to the subject. In one embodiment, the pharmaceutical composition consists of fasudil. Alternatively, the method comprises administering a pharmaceutical composition, comprising a fasudil derivative, or a pharmaceutically acceptable salt thereof, to the subject. In one embodiment, the pharmaceutical composition consists of said fasudil derivative. In one embodiment, the fasudil derivative is hydroxyl-fasudil. In another embodiment, the fasudil derivative is dimethyl-fasudil. The ALS may be sporadic ALS. Preferably, the ALS may be familial ALS.

Hence, the invention provides a method of prolonging lifetime of a subject suffering or prone to suffer from sporadic or familial ALS, wherein the method comprises administering a pharmaceutical composition, comprising or consisting of fasudil, or a fasudil derivative selected from hydroxy-fasudil and dimethyl-fasudil, or a pharmaceutically acceptable salt thereof, to the subject.

With regard to any aspect described herein, the ALS, in particular the sporadic or familial ALS, is early stage ALS as diagnosable by the Awaji-shima diagnostic criteria. It is further preferred that the administration of said composition is started presymptomatically. The pharmaceutical composition is particularly effective if the subject is a female. Preferably, the pharmaceutical composition is to be administered orally. It is further preferred that the fasudil is to be administered to the subject in a dosage of 1-12 mg/kg body weight per day, preferably in a dosage of 1.25-8 mg/kg body weight per day, such as in a dosage of 1.5-6 mg/kg body weight per day, more preferably in a dosage of 1.75-5 mg/kg body weight per day, even more preferably in a dosage of 2-4 mg/kg body weight per day, and most preferably in a dosage of 2.4-3.6 mg/kg body weight per day. In contrast thereto, the fasudil derivative is preferably to be administered to the subject in a dosage of 10-1200 ng/kg body weight per day, preferably in a dosage of 12.5-800 ng/kg body weight per day, such as in a dosage of 15-600 ng/kg body weight per day, more preferably in a dosage of 17.5-500 ng/kg body weight per day, even more preferably in a dosage of 20-400 ng/kg body weight per day, and most preferably in a dosage of 24-360 ng/kg body weight per day. Preferably, the pharmaceutical composition is formulated as a formulation with sustained release or prolonged release. For example, an improvement of the motor coordination in a subject can be determined in accordance with the ALS functional rating scale.

DETAILED DESCRIPTION OF THE PREFERRED EMBODIMENTS

In a first aspect, the invention relates to a pharmaceutical composition, comprising or consisting of 1-(5-isoquinolinesulfonyl)homopiperazine (fasudil), or a fasudil derivative selected from 1-(6-hydroxy-5-isoquinolinesulfonyl)homopiperazine (hydroxyl-fasudil) and (S)-(+)-2-Methyl-1-[(4-methyl-5-isoquinolinyl)sulfonyl]-hexahydro-1H-1,4-diazepine (dimethyl-fasudil), or a pharmaceutically acceptable salt thereof, for use in the treatment of a subject suffering or prone to suffer from sporadic or familial ALS. Likewise, the present invention provides a method of treating a subject suffering or prone to suffer from sporadic or familial ALS, wherein the method comprises administering a pharmaceutical composition, comprising or consisting of fasudil, or a fasudil derivative selected from hydroxy-fasudil and dimethyl-fasudil, or a pharmaceutically acceptable salt thereof, to the subject.

Fasudil, hydroxyl-fasudil and dimethyl-fasudil are known in the art, and described, e.g., in U.S. Pat. No. 4,678,783. Fasudil and the fasudil derivative may be used in their free forms or as salts thereof. The salt is a non-toxic salt which is pharmacologically accepted and may be formed by addition of an acid. As examples of the acid, there may be mentioned such inorganic acids as hydrochloric acid, hydrobromic acid, phosphoric acid and sulfuric acid and such organic acids as acetic acid, citric acid, tartaric acid, lactic acid, succinic acid, fumaric acid, maleic acid and methanesulfonic acid. Preferably, the salt is a hydrochloride, hydrochloride hemihydrate, hydrochloride hydrate, hydrochloride trihydrate, phosphate monobase, phosphate dibase, phosphate, hydrogen sulfate, sulfate, mesylate, ethylsulfonate, maleate, fumarate, or tartrate. More preferably, the fasudil or fasudil derivative is in form of a hydrochloride, hydrochloride hemihydrates or hydrochloride hydrate, as, e.g., described in EP 1 110 553 and U.S. Pat. No. 5,942,505, both which are incorporated herewith by reference. Moreover, fasudil and its derivatives may be used in form of their active metabolites formed in vivo. Such active metabolites are known in the art. Most preferably, fasudil or its derivative is in the form of a hydrochloride. The pharmaceutical composition may comprise fasudil, a fasudil derivative, or a pharmaceutically acceptable salt thereof. Alternatively, the pharmaceutical composition may consist of fasudil, a fasudil derivative, or a pharmaceutically acceptable salt thereof as the only active agent. However, the pharmaceutical composition may comprise further auxiliary agents, such as fillers, solvents and stabilizers such as preservatives, as well as suspending and/or dispersing agents.

Administration of the pharmaceutical composition may be effected or administered by different ways, e.g., enterally, orally (e.g., pill, tablet (buccal, sublingual, orally, disintegrating, capsule, thin film, liquid solution or suspension, powder, solid crystals or liquid), rectally (e.g., suppository, enema), via injection (e.g., intravenously, subcutaneously, intramuscularly, intraperitoneally, intradermally) via inhalation (e.g., intrabronchially), topically, vaginally, epicutaneously, or intranasally. In one embodiment, the composition is administered via injection, in particular intravenously, subcutaneously, intramuscularly, intraperitoneally, or intradermally; more particular wherein the composition is administered intravenously. Accordingly, the pharmaceutical composition may be in the form of an injectable solution, suppository, nasal spray, time-release implant, transdermal patch, or the like. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The injectable formulation may be presented in unit dosage form, e.g., in ampules or in multidose containers, or in powder form for reconstitution with a suitable vehicle, including but not limited to sterile pyrogen free water, buffer, ringer solution or dextrose solution before use. For transdermal administration, the pharmaceutical formulation may be in the form of an adhesive disc or patch, which slowly releases the active ingredient for percutaneous absorption. Optionally, such pharmaceutical formulations for transdermal delivery may be formulated along with permeation enhancers, which may be used to facilitate transdermal penetration. For rectal and vaginal routes of administration, the active ingredients may be formulated as ointments, solutions, or suppositories. For buccal administration, the pharmaceutical composition may take the form of tablets or lozenges formulated in conventional manner. However, the pharmaceutical composition may also be formulated for administration via inhalation, for example in form of a pressurized pack or nebulizer. In case of a pressurized aerosol, the dosage unit may be determined by a metered dosage unit, using a suitable propellant, e.g., dichlorodifluoromethane, trichlorofluoromethane, dichlorotetrafluoroethane, or carbon dioxide. Capsules and cartridges of e.g. gelatin for use in an inhaler or insufflator may be formulated containing a powder mix of the active agent and a suitable powder base such as lactose or starch. However, most preferably, the pharmaceutical composition is administered orally, for example, in form of a tablet or capsule. The pharmaceutical composition for oral administration may be formulated with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate), and may be coated by methods well known in the art. Liquid preparations for oral administration such as solutions, syrups or suspensions, may be prepared with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents.

Preferably, the fasudil, fasudil derivative, or a pharmaceutically acceptable salt thereof is formulated as a formulation with sustained release or prolonged release in order to provide extended plasma half-life and avoid variations in plasma concentration between dosing and eventually enhance bioavailability of the drug. For prolonged delivery, the pharmaceutical composition may be formulated as a depot preparation, for administration by implantation; e.g., subcutaneous, intradermal, or intramuscular injection. Thus, for example, the pharmaceutical composition may be formulated with suitable polymeric or hydrophobic materials (e.g., as an emulsion in an acceptable oil) or as sparingly soluble derivatives; e.g., as a sparingly soluble salt. Formulations with sustained release or prolonged release of fasudil or a fasudil derivative, in particular for oral administration, are known in the art, e.g. from WO 2005/117896, which is incorporated herewith by reference. The pharmaceutical composition may, be provided in a pack, such as a blister pack, which may contain one or more unit dosage forms, and which may be accompanied by instructions for administration.

The subject may be a mammal, such as a mouse, rat, guinea pig, dog, cat, pig, sheep, horse, or cow. Preferably, the subject is a primate, and most preferably a human. As it can be taken from the experimental section, the invention is preferably effective in females. Accordingly, in a preferred embodiment of the invention, the subject is a female.

In one embodiment, the ALS is sporadic ALS. As derivable from the term "sporadic", said type of ALS is rare and scattered in occurrence and thus patternless. However, the ALS may also be familial ALS, wherein the subject is genetically predisposed to develop ALS. The following genes have been linked with the development of ALS: Autosomal dominant: ALS-1, Ch 21q, SOD1; ALS-2, Ch 18q21; ALS-4, Ch 9q34, Senataxin; ALS-6, Ch 16p11, FUS; ALS-7, Ch 20p; ALS-9, Ch 20q13, VAPB; ALS-9, Ch 14q11, Angiogenin; ALS-10, Ch 1p36, TARDBP; ALS-11, Ch 6q21, FIG4 mutations; ALS-12, Ch 10p15, Optineurin variants or mutations; Ch 12q24, D-Amino acid oxidase mutation; Ch 9p13, VCP mutations; ALS-FTLD, Ch 9q21, Unknown gene. Autosomal recessive: ALS-2, Ch 2q33, Alsin, ALS-5, Ch 15q21, Spatacsin; ALS-12, 10p15, Optineurin. For a review, see de Carvalho & Swash (2011), which is incorporated herewith by reference. Subjects who are suspected to have or develop ALS are commonly referred to herein as subjects prone to suffer from ALS. As shown in the examples, it is advantageous to start treatment of ALS in accordance with the present invention as early as possible. Therefore, the treatment using the pharmaceutical composition according to the invention is preferably started presymptomatically. This may be the case if the subject is suspected to have ALS, although no final conclusion could be drawn, or if the subject is prone to suffer from ALS.

ALS is difficult to diagnose, although certain biomarkers have been reported to correlate with ALS (cf. Carvalho & Swash (2011); section headed "Biomarkers in amyotrophic lateral sclerosis"). ALS causes muscle weakness and atrophy throughout the body caused by degeneration of the upper and lower motor neurons. The earliest symptoms of ALS are typically obvious weakness and/or muscle atrophy. Other presenting symptoms include muscle fasciculation (twitching), cramping, or stiffness of affected muscles; muscle weakness affecting an arm or a leg; and/or slurred and nasal speech. The parts of the body affected by early symptoms of ALS depend on which motor neurons in the body are damaged first. Patients with the leg onset form may experience awkwardness when walking or running or notice that they are tripping or stumbling, often with a "dropped foot" which drags gently along the ground. Arm-onset patients may experience difficulty with tasks requiring manual dexterity such as buttoning a shirt, writing, or turning a key in a lock. Indeed, the presence of upper and lower motor neuron signs in a single limb is strongly suggestive of ALS. Electromyography (EMG) is a special technique that detects electrical activity in muscles, and certain EMG findings can support the diagnosis of ALS.

The use of electrophysiological data in ALS diagnosis was reviewed at a consensus conference held in Awaji-shima, Japan in 2006. It was recommended that electrophysiological findings should be taken as equivalent to clinical assessment in the recognition of lower motor neuron involvement. Further, in the context of a suspected clinical diagnosis of ALS, fasciculation potentials (FPs) should be taken as equivalent to fibrillation potentials (fibs) and positive sharp waves (sw) in recognizing denervation, in particular in strong limb muscles and in cranial-innervated muscles. Finally, the importance of searching for instability in fasciculation potentials and in motor unit potentials (MUP) in ALS was stressed. The earlier topographic criteria set out in the El Escorial criteria were unchanged. The Awaji-shima consensus recommendations for the application of electrophysiological tests to the diagnosis of ALS are as follows:

1. Principles (from the Airlie House Criteria)
    The diagnosis of amyotrophic lateral sclerosis [ALS] requires
    (A) the presence of (1) evidence of lower motor neuron (LMN) degeneration by clinical, electrophysiological or neuropathological examination; (2) evidence of upper motor neuron (UMN) degeneration by clinical examination; and (3) progressive spread of symptoms or signs within a region or to other regions, as determined by history, physical examination, or electrophysiological tests;
(B) the absence of (1) electrophysiological or pathological evidence of other disease processes that might explain the signs of LMN and/or UMN degeneration, and (2) neuroimaging evidence of other disease processes that might explain the observed clinical and electrophysiological signs.

2. Diagnostic Criteria

Clinically definite ALS is defined by clinical or electrophysiological evidence by the presence of LMN and/or UMN signs in the bulbar region and at least two spinal regions or the presence of LMN and UMN signs in three spinal regions.

Clinically probable ALS is defined on clinical or electrophysiological evidence by LMN and UMN signs in at least two regions with some UMN signs necessarily rostral to (above) the LMN signs.

Clinically possible ALS is defined when clinical or electrophysiological signs of UMN and LMN dysfunction are found in only one region; or UMN signs are found alone in two or more regions; or LMN signs are found rostral to UMN signs. Neuroimaging and clinical laboratory studies will have been performed and other diagnoses must have been excluded.

The criteria for detection of neurogenic change by needle electromyography (EMG) in the diagnosis of ALS are as follows:

1. For the evaluation of LMN disease in ALS in any given body region clinical and electrophysiological abnormalities have equal diagnostic significance.
2. EMG features of chronic neurogenic change must be found, for example
   a. MUPs of increased amplitude and increased duration, usually with an increased number of phases, as assessed by qualitative or quantitative studies.
   b. Decreased motor unit recruitment, defined by rapid firing of a reduced number of motor units. In limbs affected by clinical features of significant UMN abnormalities, rapid firing may not be achieved.
   c. Using a narrow band pass filter (500 Hz to 5 kHz) unstable and complex MUPs will be observed in most cases of ALS.
3. In ALS fbs-sw are usually recorded in strong, non-wasted, muscles.
4. In the presence of chronic neurogenic change on needle EMG in ALS, fasciculation potentials (FPs), preferably of complex morphology, are equivalent to fibrillations and positive sharp waves (fibs-sw) in their clinical significance.

Complex FPs: one feature of polyphasic (>4 phases), increased duration, or increased amplitude compared to normal values for MUPs in the muscle studied. Complex FPs may be unstable.

Fibs-sw: (AANEM definition) duration<5 ms, amplitude<1 mV, discharge frequency 1-50 Hz.

Unstable MUPs: use low band pass filter setting >500 Hz; superimpose sequence of consecutive motor unit discharges, and look for increased jitter (jiggle) and impulse blocking.

Chronic neurogenic change: MUPs of increased duration, increased amplitude, and often with increased phases. A decreased interference pattern characterized by increasing firing rate of remaining motor units, and increased envelope amplitude of the interferential pattern.

Other disorders may be excluded by nerve conduction studies, wherein the following are compatible with ALS:

Normal SNAP amplitude and sensory conduction velocities (CV) in the absence of concomitant entrapment or other neuropathies. Mildly reduced SNAP amplitudes and CVs in the presence of neuropathy of identified aetiology are acceptable.

Motor CV >75% of the lower limit of normal, and minimum F-wave latency <130% of the upper limit of normal.

Distal CMAP latency and duration <150% of normal.

Absence of conduction block (CB) and of pathological temporal dispersion, as defined by baseline-negative CMAP area reduction on proximal versus distal stimulation >50% when distal baseline-negative peak CMAP amplitude is large enough to allow such assessment (usually >1 mV). A proximal negative peak CMAP duration <30% of the distal value suggests CB.

The utility of the Awaji-shima revision of the Airlie House diagnostic criteria has been proven successful in several studies, wherein it was found that the diagnostic sensitivity improved when the Awaji-shima criteria were applied, without loss of specificity. Utilizing the Awaji-shima criteria allows an earlier diagnosis of ALS, and thus an earlier treatment of ALS. For a review, see de Carvalho et al. (2008), which is incorporated herewith by reference. The skilled in the art knows how to perform these tests. As shown in the experimental section, treatment with fasudil and/or a fasudil derivative appears to be most effective if the ALS is in an early stage, that is before or when first electrophysiological signs, which are predictive of ALS, are detectable. Hence, the present invention is particularly useful if the subject is diagnosed for suspected ALS or possible ALS. The invention is further particularly useful, if the sporadic or familial ALS is early stage ALS as diagnosable by the Awaji-shima diagnostic criteria, in particular as detectable by needle EMG, more particular as detectable by EMG features of chronic neurogenic change as defined in point 2 above, most preferably by EMG features of chronic neurogenic change as defined in point 2a, point 2b, point 2c, point 2a and 2b, point 2a and 2c, point 2b and 2c, or point 2a and 2b and 2c. Although it might be helpful, in the context of the present invention it is not absolutely necessary to exclude other disorders.

In the experimental section, the inventors monitored the drinking amounts of mice that were determined with 0.2 ml/g body weight/day prior to treatment initiation. To reach sufficient CSF levels of Fasudil the inventors administered Fasudil (LC Labs, Woburn, USA; product number F-4660) at a low concentration of 15 mg (Fas30) or at a high concentration of 50 mg (Fas100) in 100 ml drinking water. Control groups received the respective amount of isotonic drinking water termed as vehicle (Veh). Accordingly, the mice received a dosage of 0.2 ml/g body weight/day×(15 mg/100 ml)=0.03 mg/g body weight=30 mg/kg body weight (Fas30); and 0.2 ml/g body weight/day×(50 mg/100 ml)=100 mg/kg body weight (Fas100), respectively.

Dose translation from one animal to another animal or from an animal to human studies is well known in the art, cf. Reagan-Shaw et al. (2007), which is incorporated herewith by reference, in particular FIG. 1 and Table 1. Accordingly, the human equivalent dose (HED; mg per kg body weight) may be calculated as follows: HED (mg/kg)=Animal dose (mg/kg)×(Animal Km/Human Km). The Km factor, body weight (kg) divided by body surface area (BSA; $m^2$), is used to convert the mg/kg dose used in a study to an mg/$m^2$ dose. Exemplary Km values based on average BSA calculations on data from FDA Draft Guidelines are given below.

| Species | Weight (kg) | BSA (m²) | Km factor |
|---|---|---|---|
| Human | | | |
| Adult | 60 | 1.6 | 37 |
| Child | 20 | 0.8 | 25 |
| Baboon | 12 | 0.6 | 20 |
| Dog | 10 | 0.5 | 20 |
| Monkey | 3 | 0.24 | 12 |
| Rabbit | 1.8 | 0.15 | 12 |
| Guinea Pig | 0.4 | 0.05 | 8 |
| Rat | 0.15 | 0.025 | 6 |
| Hamster | 0.08 | 0.02 | 5 |
| Mouse | 0.02 | 0.007 | 3 |

In view of the experimental data given below, if the pharmaceutical composition comprises or consists of fasudil or a pharmaceutically acceptable salt thereof, the fasudil is to be administered to the subject in a dosage of 1-12 mg/kg body weight per day, preferably in a dosage of 1.25-8 mg/kg body weight per day. Nevertheless, it could be demonstrated that the Fas30 treatment was particularly effective. Accordingly, in a preferred embodiment, fasudil is to be administered in a dosage of 1.5-6 mg/kg body weight per day, preferably in a dosage of 1.75-5 mg/kg body weight per day, more preferably in a dosage of 2-4 mg/kg body weight per day, and most preferably in a dosage of 2.4-3.6 mg/kg body weight per day.

Alternatively, the pharmaceutical composition may comprise or consist of a fasudil derivative, in particular selected from hydroxy-fasudil and dimethyl-fasudil, or a pharmaceutically acceptable salt thereof. It is known in the art that the effect of fasudil derivatives such as hydroxy-fasudil and dimethyl-fasudil is 10 to 100 times higher as compared to fasudil. Based on the data for fasudil, it is thus preferred that the fasudil derivative is administered in a dosage of $1/10$-$1/100$ of that of fasudil. In particular, it is preferred that the fasudil derivative is administered to the subject in a dosage of 10-1200 ng/kg body weight per day, preferably in a dosage of 12.5-800 ng/kg body weight per day, such as in a dosage of 15-600 ng/kg body weight per day, more preferably in a dosage of 17.5-500 ng/kg body weight per day, even more preferably in a dosage of 20-400 ng/kg body weight per day, and most preferably in a dosage of 24-360 ng/kg body weight per day. The actual dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

Further, it could be demonstrated that fasudil is capable of improving the motor coordination in a subject suffering from ALS, or in a subject prone to suffer from ALS. In view of this finding, it is plausible that the same advantageous effect can be achieved with a pharmaceutically acceptable salt of fasudil, or with a fasudil derivative, e.g. with hydroxyl-fasudil or dimethyl-fasudil, or a pharmaceutically acceptable salt of said derivative.

Accordingly, in a further aspect, the invention provides a method of improving motor coordination in a subject suffering or prone to suffer from sporadic or familial ALS, wherein the method comprises administering a pharmaceutical composition, comprising or consisting of fasudil, or a fasudil derivative selected from hydroxy-fasudil and dimethyl-fasudil, or a pharmaceutically acceptable salt thereof, to the subject.

The preferred embodiments according to this additional aspect are identical with the preferred embodiments of the first aspect, and apply likewise. In particular, it is preferred that the ALS, such as the sporadic or familial ALS, is early stage ALS as diagnosable by the Awaji-shima diagnostic criteria, as further defined above. Further, the administration of the pharmaceutical composition is started presymptomatically, and the subject is preferably a female. Although the pharmaceutical composition may be administered by various routes, it is particularly preferred that the pharmaceutical composition is administered orally. With regard to the dosage, if the pharmaceutical composition comprises or consists of fasudil, it is preferred that the fasudil is administered to the subject in a dosage of 1-12 mg/kg body weight per day, preferably in a dosage of 1.25-8 mg/kg body weight per day, such as in a dosage of 1.5-6 mg/kg body weight per day, more preferably in a dosage of 1.75-5 mg/kg body weight per day, even more preferably in a dosage of 2-4 mg/kg body weight per day, and most preferably in a dosage of 2.4-3.6 mg/kg body weight per day. Alternatively, if the pharmaceutical composition comprises or consists of a fasudil derivative, such as hydroxy-fasudil or dimethyl-fasudil, the fasudil derivative is administered to the subject in a dosage of 10-1200 ng/kg body weight per day, preferably in a dosage of 12.5-800 ng/kg body weight per day, such as in a dosage of 15-600 ng/kg body weight per day, more preferably in a dosage of 17.5-500 ng/kg body weight per day, even more preferably in a dosage of 20-400 ng/kg body weight per day, and most preferably in a dosage of 24-360 ng/kg body weight per day. Finally, it is further preferred that the fasudil, fasudil derivative, or pharmaceutically acceptable salt thereof is formulated as a formulation with sustained release or prolonged release, as further described above.

The improvement of the motor coordination in a subject may be determined in accordance with a score as defined by the ALS functional rating scale, as revised in accordance with Cedarbaum 1999 (Cedarbaum, Stambler et al. 1999):

1. Speech: Normal speech processes (4); Detectable speech disturbance (3); Intelligible with repeating (2); Speech combined with nonvocal communication (1); Loss of useful speech (0)
2. Salivation: Normal (4); Slight but definite excess of saliva in mouth, may have nighttime drooling (3); Moderately excessive saliva, may have minimal drooling (2); Marked excess of saliva with some drooling (1); Marked drooling, requires constant tissue or handkerchief
3. Swallowing: Normal eating habits (4); Early eating problems—occasional choking (3); Dietary consistency changes (2); Needs supplemental tube feeding (1); NPO—exclusively parenteral or enteral feeding (0)
4. Handwriting: Normal (4); Slow or sloppy—all words are legible (3); Not all words are legible (2); Able to grip pen but unable to write (1); Unable to grip pen (0)
5. Cutting food and handling utensils:
    a. Patients without gastrostomy: Normal (4); Somewhat slow and clumsy, but no help needed (3); Can cut most foods, although clumsy and slow, some help needed (2); Food must be cut by someone, but still can feed slowly (1); Needs to be fed (0)
    b. Patients with gastrostomy: Normal function (4); Clumsy but able to perform all manipulations independently (3); Some help needed with closures and fasteners (2); Provides minimal assistance to caregiver (1); Unable to perform any aspect of task (0)
6. Dressing and hygiene: Normal function (4); Independent and complete self-care with effort or decreased efficiency (3); Intermittent assistance or substitute methods (2); Needs attendant for self-care (1); Total dependence (0)
7. Turning in bed and adjusting bed clothes: Normal (4); Somewhat slow and clumsy, but no help needed (3); Can turn alone or adjust sheets, but with great difficulty (2); Can initiate, but not turn or adjust sheets alone (1); Helpless (0)
8. Walking: Normal (4); Early ambulation difficulties (3); Walks with assistance (2); Nonambulatory functional movement (1); No purposeful leg movement (0)
9. Climbing stairs: Normal (4); Slow (3); Mild unsteadiness or fatigue (2); Needs assistance (1); Cannot do (0)
10. Dyspnea: None (4); Occurs when walking (3); Occurs with one or more of the following: eating, bathing, dressing (2); Occurs at rest, difficulty breathing when either sitting or lying (1); Significant difficulty, considering using mechanical respiratory support (0)
11. Orthopnea: None (4); Some difficulty sleeping at night due to shortness of breath, does not routinely use more than two pillows (3); Needs extra pillows in order to sleep (more than two) (2); Can only sleep sitting up (1); Unable to sleep (0)
12. Respiratory insufficiency: None (4); Intermittent use of BiPAP (3); Continuous use of BiPAP during the night (2); Continuous use of BiPAP during the night and day (1); Invasive mechanical ventilation by intubation or tracheostomy (0)

In a final aspect, the present invention provides a method of prolonging lifetime of a subject suffering or prone to suffer from sporadic or familial ALS, wherein the method comprises administering a pharmaceutical composition, comprising or consisting of fasudil, or a fasudil derivative selected from hydroxy-fasudil and dimethyl-fasudil, or a pharmaceutically acceptable salt thereof, to the subject.

The preferred embodiments according to this additional aspect are identical with the preferred embodiments of the first aspect, and apply likewise. In particular, it is preferred that the ALS, such as the sporadic or familial ALS, is early stage ALS as diagnosable by the Awaji-shima diagnostic criteria, as further defined above. Further, the administration of the pharmaceutical composition is started presymptomatically, and the subject is preferably a female. Although the pharmaceutical composition may be administered by various routes, it is particularly preferred that the pharmaceutical composition is administered orally. With regard to the dosage, if the pharmaceutical composition comprises or consists of fasudil, it is preferred that the fasudil is administered to the subject in a dosage of 1-12 mg/kg body weight per day, preferably in a dosage of 1.25-8 mg/kg body weight per day, such as in a dosage of 1.5-6 mg/kg body weight per day, more preferably in a dosage of 1.75-5 mg/kg body weight per day, even more preferably in a dosage of 2-4 mg/kg body weight per day, and most preferably in a dosage of 2.4-3.6 mg/kg body weight per day. Alternatively, if the pharmaceutical composition comprises or consists of a fasudil derivative, such as hydroxy-fasudil or dimethyl-fasudil, the fasudil derivative is administered to the subject in a dosage of 10-1200 ng/kg body weight per day, preferably in a dosage of 12.5-800 ng/kg body weight per day, such as in a dosage of 15-600 ng/kg body weight per day, more preferably in a dosage of 17.5-500 ng/kg body weight per day, even more preferably in a dosage of 20-400 ng/kg body weight per day, and most preferably in a dosage of 24-360 ng/kg body weight per day. Finally, it is further preferred that the fasudil, fasudil derivative, or pharmaceutically acceptable salt thereof is formulated as a formulation with sustained release or prolonged release, as further described above.

The following examples are intended to further illustrate the invention.

EXAMPLES

Example 1

Figure 1:
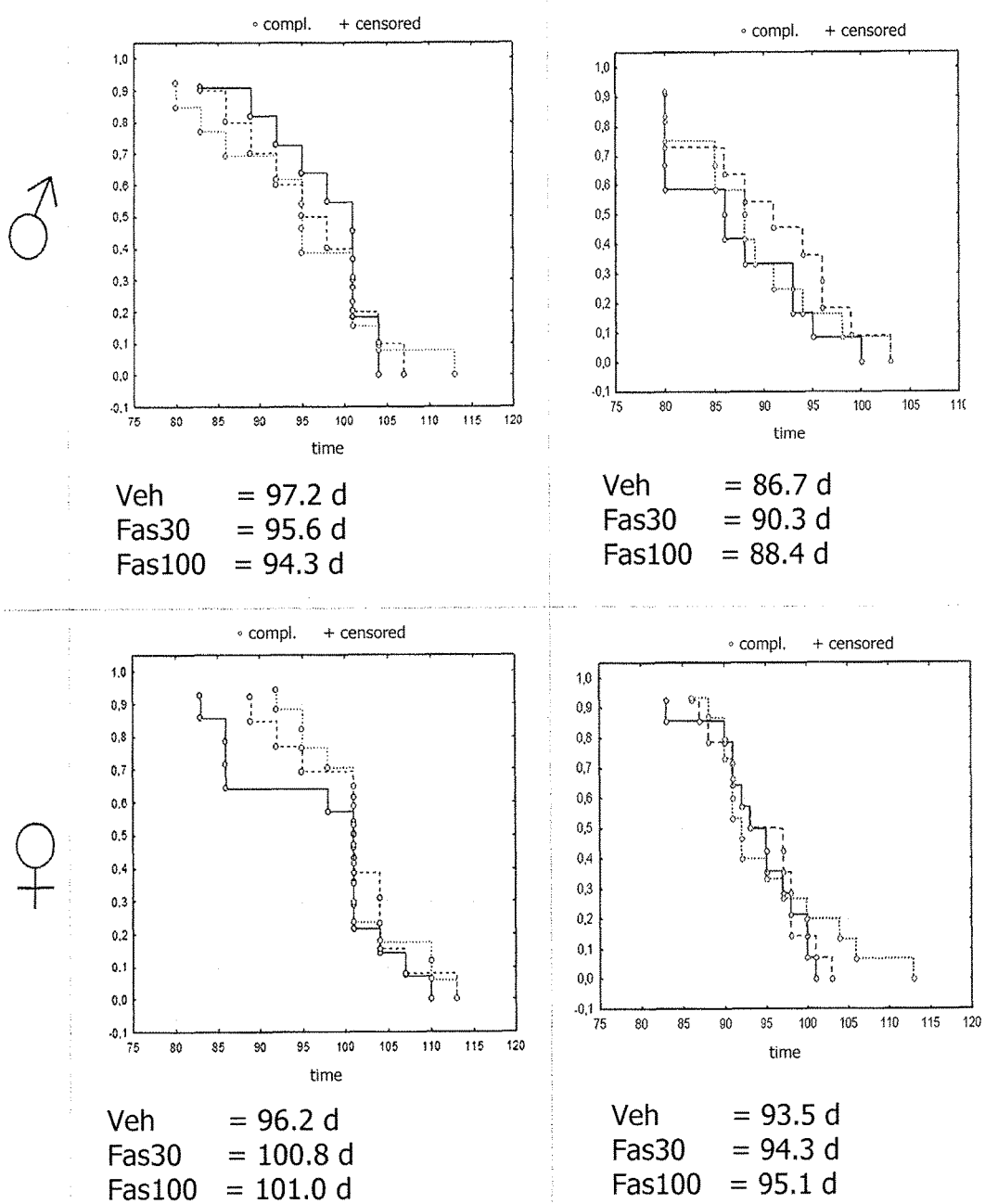
FIG. 1: Kaplan-Meier time-to-failure plot for onset of symptomatic neurological disease in SOD1$^{G93A}$ mice treated from d50 (A) or from d80 (B) on differentiated by gender. VEH: solid line; Fas30: dashed line; Fas100: pointed line.

Material and Methods
Animals

All animal experiments were carried out according to the regulations of the local animal research council and legislation of the State of Lower Saxony. High-copy B6SJL-Tg (SOD1*G93A)1Gur/J were obtained from Jackson Labs (Stock Number 002726; Bar Harbor, USA) that had originally been produced by Gurney et al. (Gurney, Pu et al. 1994). The colony was maintained by crossing C57BL/6 males harboring the transgene with wild-type SJL females. To verify presence of the transgene in the F1 progeny, tail biopsies were collected from 14-day-old pups and genotyped using PCR. At the age of 35-45 days mice were moved to the testing facility to acclimate to the new environment with a 12-h light/dark cycle before being assigned to a study.
Experimental Groups At 50 days (presymptomatic, d50) or 80 days of age (symptomatic, d80) mice were separated into Fasudil-30 (Fas30)- and Fasudil-100 (Fas100)-Treatment or Vehicle Control (Veh) groups. Prior to any treatment, groups were constituted so as to minimize between-group variability by using the following criteria. Groups were balanced with respect to gender and body weight within gender. In addition, groups were age-matched and littermate-matched. Each male and female in the Treatment group had a corresponding male and female littermate in the Vehicle Control group. The study was observer-blinded.
Treatments Before treatment initiation the inventors monitored the drinking amounts of mice that were determined with 0.2 ml/g body weight/day. To reach sufficient CSF levels of Fasudil the inventors administered Fasudil (LC Labs, Woburn, USA; product number F-4660) at a low concentration of 15 mg (Fas30) or at a high concentration of 50 mg (Fas100) in 100 ml drinking water. Control groups received the respective amount of isotonic drinking water termed as vehicle (Veh). CSF analysis after sub-occipital cistern magna puncture demonstrated that Fasudil readily crossed the blood-brain-barrier (data not shown).

Chronic oral treatment with a low dose of Fasudil (F30) or a high dose of Fasudil (F100) was started either presymptomatically at day 50 or symptomatically at day 80 and continued until death.
Monitoring Disease Progression Neurological Score. Neurological scores were assessed every three days for each mouse from 50 days of age. The neurological score employed a scale of 0 to 4 that had been developed in ALS mouse trials before. Score criteria used to assign each score level were:
4 Full extension of hind legs away from lateral midline when mouse is suspended by its tail, and mouse can hold this for 2 seconds, suspended 2-3 times.
3 Collapse or partial collapse of leg extension towards lateral midline (weakness) or trembling of hind legs during tail suspension.
2 Toes curl under at least twice during walking of 10 cm, or any part of foot is dragging along cage bottom/table.
1 Rigid paralysis or minimal joint movement, foot not being used for forward motion*.
  * If score criterion 2 is reached, food pellets are left on bedding and water is additionally placed in a well on the bedding.
0 Mouse cannot right itself within 30 seconds from either side.

Body Weight. Body weight is a sensitive indicator of any malaise that might result from chronic drug treatment and of motor impairment that occurs during disease progression. Body weight measurements were recorded every three days for each animal beginning at 50 days of age.

Survival. Date and cause of death were recorded for each mouse. For humane reasons, animals are closely monitored and sacrificed as moribund prior to actual death using criteria for severe moribundity. To determine duration of survival reliably and humanely, the moribund state, defined as the inability of mice to right themselves 30 seconds after being placed on a side (a neurological score of 4) was used. The moribund mice were scored as "dead", and were euthanized using carbon dioxide.

Disease duration. This parameter was selected in order analyze the treatment effects under a clinically relevant situation of the time from disease onset until death.
Immunohistochemistry of Spinal Cord, Sciatic Nerve and Gastrocnemius Muscle Sections After deep anaesthesia, mice were transcardially perfused with PBS solution followed by 4% paraformaldehyde. Spinal cords, sciatic nerves and gastrocnemius muscles were removed. Spinal cords and gastrocnemius muscles were then postfixed for 2 h in 4% paraformaldehyde. Thereafter, the tissue was dehydrated in 30% sucrose overnight and kept at −20° C. until further processing. Coronal sections of the lumbar spinal cord (L3-L6) (20 μm) and horizontal sections of the tibial muscle (35 μm) were prepared using a Leica Kryostat and collected on gelatine-coated glass slides.

Spinal cord sections selected for immunohistochemical processing were first rehydrated. Then antigen-retrieval was performed for 4 h in TBS at 60° C. for later GFAP or Iba1 labeling and for 30 min in sodium citrate (pH 9.0) at 80° C. for later ChAT labeling. After washing for one time in PBS the sections were incubated at room temperature either in PBS and 10% of normal goat serum for later GFAP labeling or in PBS and 5% normal donkey serum for later ChAT labeling to block unspecific binding. The primary antibodies (anti-ChAT 1:100, AB144 P, Millipore; anti-GFAP 1:200, DAKO; anti-Iba1 1:500, WAKO, Osaka, Japan) were applied at 4° C. for one night for GFAP and for three nights for ChAT. The secondary antibodies (Cy3 anti-goat or Cy2/Dylight anti rabbit; both Dianova) were applied on separate sections 1:300 for 1 h at room temperature. Then a nuclear counter-stain with DAPI (4,6-diamidino-2-phenylindole) (Sigma-Aldrich) was performed before mounting in Moviol (Hoechst, Frankfurt, Germany).

Sciatic nerves were removed separately and postfixed for 24 h in 4% paraformaldehyde. For embedding, the samples were fixed in 3% Glutaraldehyd in PBS for 3 h at 4° C., then postfixed in 1% Osmiumoxid in PBS for 1 h at 4° C. After three washing steps the nerves were embedded in Araldit and Propylenoxide with a ratio of first 1:1 and then 2:1, each for 35 min. Before putting into a flat mould for drying and harding, Propylenoxide had to evaporate under a hood for 1 h. The sciatic nerves embedded in araldit blocks were cut with a Microtom (Leica Ultracut) into semithin sections (380 nm) and were collected on gelatine coated glass slides. Then they were stained with Richardson-Solution (2:1:1 of 1% Azur-2-solution, 2% Methylbluesolution and 1% Boraxsolution (Di-Natriumtetraborat-10-hydrat)). After washing in distilled water, slices were dried and mounted in Depex.

Gastrocnemius muscle sections were rehydrated and permeabilization was done for 2 h at room temperature in PBS, 5% IgG free and protease free Bovine Serum Albumin (Jackson ImmunoResearch Laboratories, Lot 91563), 0.5% Trition X-100 (Molecular Sigma biology, T-8787). The primary antibodies (rabbit anti-Neurofilament M, 1:1000, Millipore, AB1987; rabbit anti-VAChT, 1:1000, Sigma-Aldrich, V5387) were applied together at 4° C. overnight in 1% BSA, 0.25% Triton X-100. After extensive washing in PBS 1% BSA, the secondary antibody (anti-rabbit Alexa fluo 488, 1:300; A11034, Invitrogen Molecular Probes) was incubated with α-bungarotoxin Alexa Fluor 594 conjugate (1:1000, B13423, Invitrogen Molecular Probes) for 90 min in PBS, 1% BSA at room temperature. Finally the muscle sections were washed for three times in PBS, once in water and were then mounted in Moviol (Hoechst, Frankfurt, Germany).

Quantitative Evaluation of Spinal Cord Motoneurons, Astro- and Microglia, Sciatic Nerve Axons and NMJ In order to quantify motoneuron numbers in coronal cryosections from the lumbar spinal (L3-L6) cord first the area of the ventral horn was defined according to the criteria from Kong et al. (Kong and Xu 1998). Cells were counted as motoneurons if they were located in the ventral horn, had a clearly identifiable nucleolus, were at least 200 μm² in size and were ChAT-positive (Pitzer, Kruger et al. 2008). At least five sections per mouse spinal cord that were 100 μm apart over a length of at least 500 μm isolated from the lumbar spinal cord were counted. In the d50 treatment group analyzed at death, a total of 20 mice was counted from the vehicle (3 male, 3 female), Fas30 (3 male, 3 female), Fas100 (3 male, 3 female) and wildtype (1 male, 1 female) group. In the d80 treatment group analyzed at death, a total of 20 mice was counted from the vehicle (3 male, 3 female), Fas30 (3 male, 3 female), and Fas100 (3 male, 3 female) and wildtype (1 male, 1 female) group. In the d50 treatment group analyzed at d100, a total of 20 mice was counted from the vehicle (3 male, 3 female), Fas30 (3 male, 3 female), Fas100 (3 male, 3 female) and wildtype (1 male, 1 female) group.

Astrogliosis and microgliosis were evaluated by the quantification of GFAP or Iba1 positive cells in the ventral horn of lumbar spinal cord sections, respectively. Again, the area of the ventral horn was defined and GFAP or Iba1 positive cells were manually counted. In the d50 treatment group analyzed at death, a total of 20 mice was counted from the vehicle (3 male, 3 female), Fas30 (3 male, 3 female), Fas100 (3 male, 3 female) and wildtype (1 male, 1 female) group. In the d50 treatment group analyzed at d100, a total of 20 mice was counted from the vehicle (3 male, 3 female), Fas30 (3 male, 3 female), Fas100 (3 male, 3 female) and wildtype (1 male, 1 female) group.

For the evaluation of microglia morphology at least 10 randomly chosen cells per ventral horn were examined with a 63× objective. Cells were classified as "thin ramified", "stouter ramified" and "rounded" according to a recent morphologic description by Graeber et al. (Graeber, M. B. (2010) Science 330(6005): 783-788). A ramified cell was defined as a cell that has at least 2 processes that are at least twice the size of cell body. Thin ramified cells were defined to have a small diameter of ramifications (<0.5 μm) and a small cell soma diameter (<5 μm). Stoutly ramified cells were defined with thicker ramifications (>0.5 μm) and a larger cell soma diameter (>5 μm). Round cells were defined to exhibit no processes and a round appearance.

Semithin cuts of sciatic nerve axons were evaluated from light microscopy images for axonal numbers and axoplasm size with the semi-automated counting and size measuring tool of the Image J software. In the d50 treatment group analyzed at d100, a total of 17 female mice were counted from vehicle (5), Fas30 (7), and wildtype (5).

In order to evaluate the integrity of NMJ, muscular sections, that had been labeled for the distal axonal and endplate innervating structures with anti-Neurofilament M/Alexa 488 and anti-VAChT/Alexa 488 and for endplates with α-bungarotoxin/rhodamine, respectively, were examined under a fluorescence microscope. End-plates were scored as "innervated" if there was complete overlap with the axon terminal, or "denervated" if the end-plate was not associated with an axon. Some neuromuscular junctions that presented a preterminal axon only, or showed only a partial overlap between end-plate and terminal were labeled as "intermediate". For each muscle 4 sections of its distal, middle and proximal part that were 140 μm apart over a length of at least 560 μm and contained at least 10 endplates per section were evaluated.

Electrophysiology

Nerve conduction velocities (NCVs) and compound muscle action potentials (CMAPs) were determined at 100 days of age as previously described (Meyer zu Horste, Prukop et al. 2007). Briefly, mice were anaesthetized using an intraperitoneal injection of ketamin (100 mg/kg) and xylazin (5 mg/kg), while body temperature was maintained constantly using a heating plate connected to a rectal temperature sensor (cma, Stockholm, Sweden). Tail NCV proved to be more reproducible than recordings from the sciatic nerve which had to be exposed surgically. Stimulation was performed with increasing voltage until supramaximal stimulation was achieved. Maximum CMAP voltage was recorded from the tail muscle with fine subcutaneous needle electrodes using a Jaeger-Toennies Neuroscreen instrument (Würzburg, Germany). CMAP amplitudes were calculated as peak to peak. NCV was calculated from distance and motor latency differences between proximal and distal stimulations.

Statistical Analysis

The data were then analyzed using Kaplan-Meier survival fit analysis with the Log-Rank and Wilcoxon tests for statistical significance. Cox proportional hazards analysis was also performed to determine hazard ratios and test for statistical significance of their differences using the Effect Likelihood Chi Square test. Statistical analyses were performed using Statistica 9.1 (StatSoft, Hamburg, Germany). P-values less than 0.05 were taken to be statistically significant.

Results

Disease Onset is not Modified by Pre- or Symptomatic Fasudil Treatment

Onset of disease is defined as reaching neurological score 3 (collapse or partial collapse of leg extension towards lateral midline (weakness) or trembling of hind legs during tail suspension). There was no statistically significant difference in the onset of disease in animals treated from d50 or from d80 differentiated by gender (FIG. 1).

Figure 2:
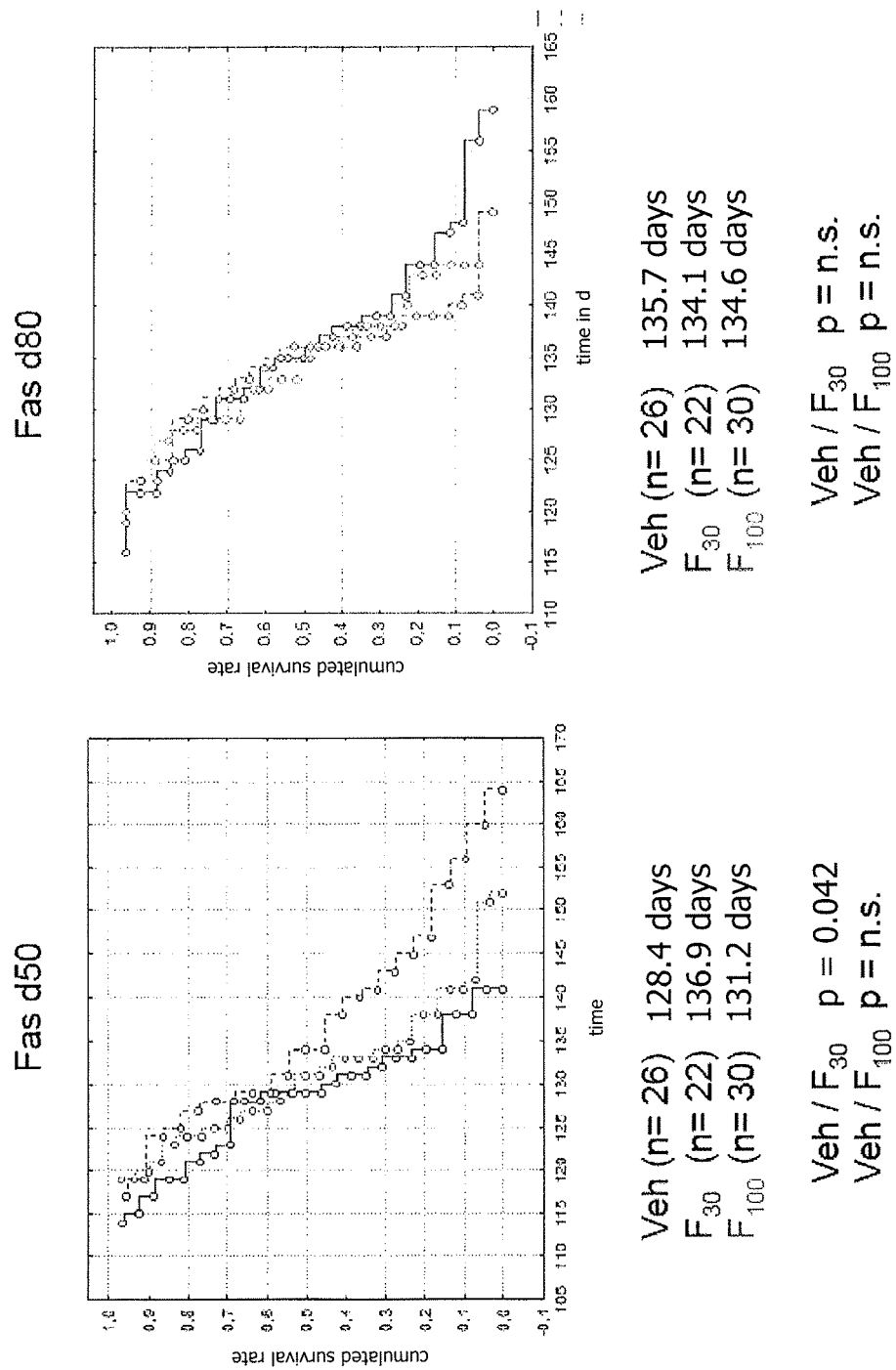
FIG. 2: Kaplan-Meier survival plot for age at death in SOD1$^{G93A}$ mice. VEH: solid line; Fas30: dashed line; Fas100: pointed line.

Survival and Disease Duration are Prolonged in Presymptomatically Treated SOD G93A Mice The proportion of mice surviving over time non-differentiated by gender is shown in FIG. 2. Whereas both symptomatic (d80) Fas30 and Fas100 groups did not show a statistically significant difference in survival proportions over time, the presymptomatic (d50) Fas30 group profited significantly from the treatment.

If differentiated by gender, the female presymptomatic Fas30 group was significantly profiting from treatment surviving in average for 141.8 days compared to 130.4 days in the control group. Presymptomatic Fas30 treatment for males showed a trend in prolongation of survival.

If Fasudil treatment was initiated only from a symptomatic time point on, it was not able to prolong survival in either female or male group.

Disease duration is defined as beginning from the appearance of the first clinical symptoms until death. In this parameter the presymptomatically treated female mice showed a prolonged time. The symptomatically treated groups did not show any significant alterations.

The clinical monitoring of the therapy study consisted of clinical neurologic scoring and body weight analysis performed every three days for all animals. Thereby, the inventors were able to exactly define the onset of disease, monitor the disease progression and determine the time of death. In presymptomatically treated animals the inventors did not observe a prolongation of disease onset. This is a common finding in many other ALS therapy studies, e.g. using Riluzole.

The criteria to terminate the therapy study (later referred to as time of death) were fulfilled if the animals had reached the terminal neurological scoring or had lost a defined percentage of the maximal body weight. This time point then reflects the survival time of the animals whereas disease duration was measured from onset of disease until time of death. The presymptomatic treatment group significantly profited from the Fas30 treatment concerning survival, whereas the effect of Fas100 was less prominent. If differentiated for gender, this survival promoting effect was most pronounced for females. Without being bound by theory, an explanation for this can be inferred already from other studies in which the inventors have tested pharmacologic ROCK inhibitors in various experimental settings before. Here, the inventors had noted an important dose-dependent effect of ROCK inhibition by Fasudil (HA-1077) and more importantly by its derivative Dimethyl-Fasudil (HA-1152) (Lingor 2007, 2008). It seemed that for these pharmacologic ROCK inhibitors an optimal concentration has always to be titrated depending on the experimental application because the therapeutic window of ROCK inhibitors seems to be limited. As an example, the regenerative potential of ROCK inhibition to increase the number of regenerating axons after optic nerve crush lesion was significantly reduced if a high intravitreal dose of Dimethylfasudil (40 µmol/l) had been applied in comparison to a medium dose (400 nmol/l) (Lingor, Teusch et al. 2007). The inventors attributed this decrease in outgrowth promoting activity to a co-inhibitory activity on growth-related kinases, such as protein kinase N, protein kinase A, mitogen- and stress-activated protein kinase 1, citron kinase or myosin light chain kinase (Davies, Reddy et al. 2000).

Figure 19:
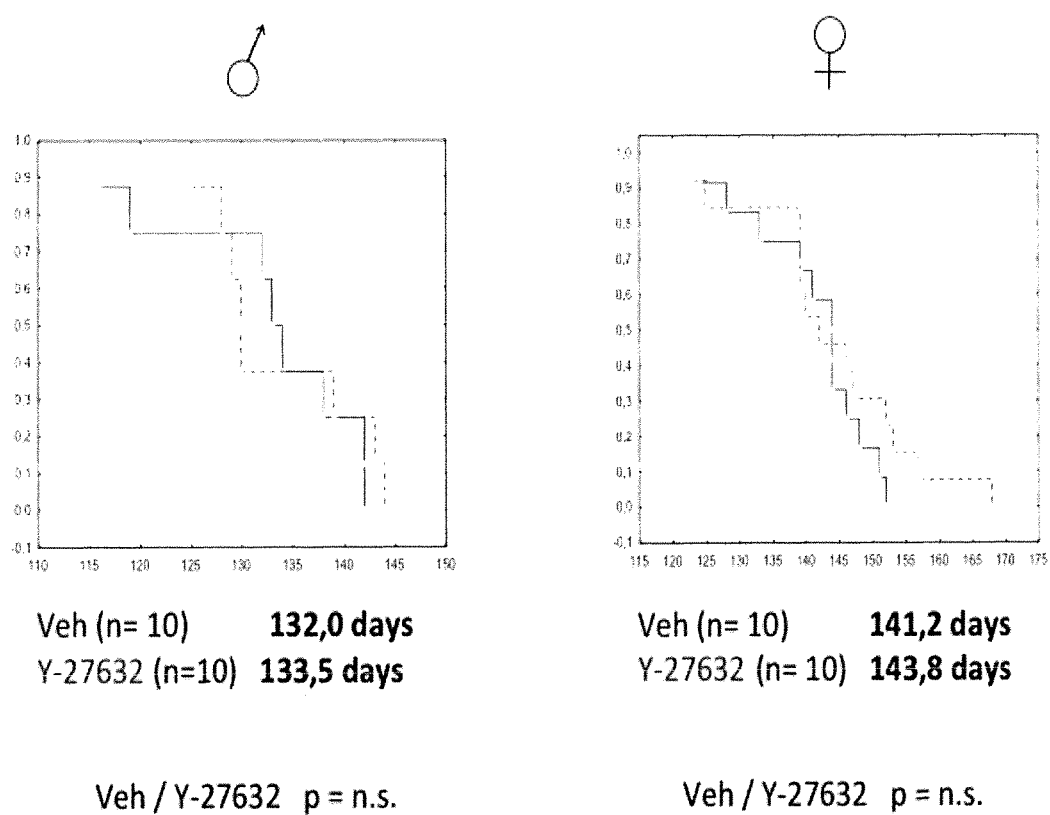
FIG. 19: Kaplan-Meier survival plot for age at death in male and female SOD1$^{G93A}$ mice presymptomatically treated with Y-27632 (10 mg/kg body weight).

Interestingly, presymptomatic ROCK inhibition with the pharmacologically more potent ROCK inhibitor Y-27632 in a dosage comparable in efficacy with Fasudil low dose did not result in survival promoting effects (FIG. 19). Thus, the beneficial effects of Fasudil on survival do not seem to be a group effect of ROCK inhibitors but is likely to be specific for Fasudil.

The symptomatic (d80) treatment was not able to improve survival in both applied Fasudil concentrations. This could be due to an already too far progressed disease process that Fasudil is not able to halt. Another possibility would be that Fasudil is not as effective against end-stage disease pathophysiology as against the early stage alterations. Whereas early stages are characterized by destruction of NMJ innervation and axonal degeneration, progression of symptomatic disease until end-stage is mainly characterized by infiltration of microglia and overall inflammation. In comparison, many other treatments that have been successful if started presymptomatically have failed if applied only at symptomatic stages. Therefore, a very early diagnosis is most relevant in this disease so that Fasudil is able to exert its beneficial effects over a longer time period.

Motor Coordination but not Overall Muscular Strength is Improved by Presymptomatic Fasudil Treatment From a patient's point of view overall survival is not the only parameter of a successful therapy. Many recent therapeutic studies in humans rather evaluate an increased time with improved quality of life. An improved motor function could be one parameter that is relevant for the quality of daily life and therefore the inventors chose two different tests to monitor motor function in the present animal model. The rotarod test evaluates fine motor coordination and is a very sensitive test for the ability to move on an unstable underground.

Figure 5:
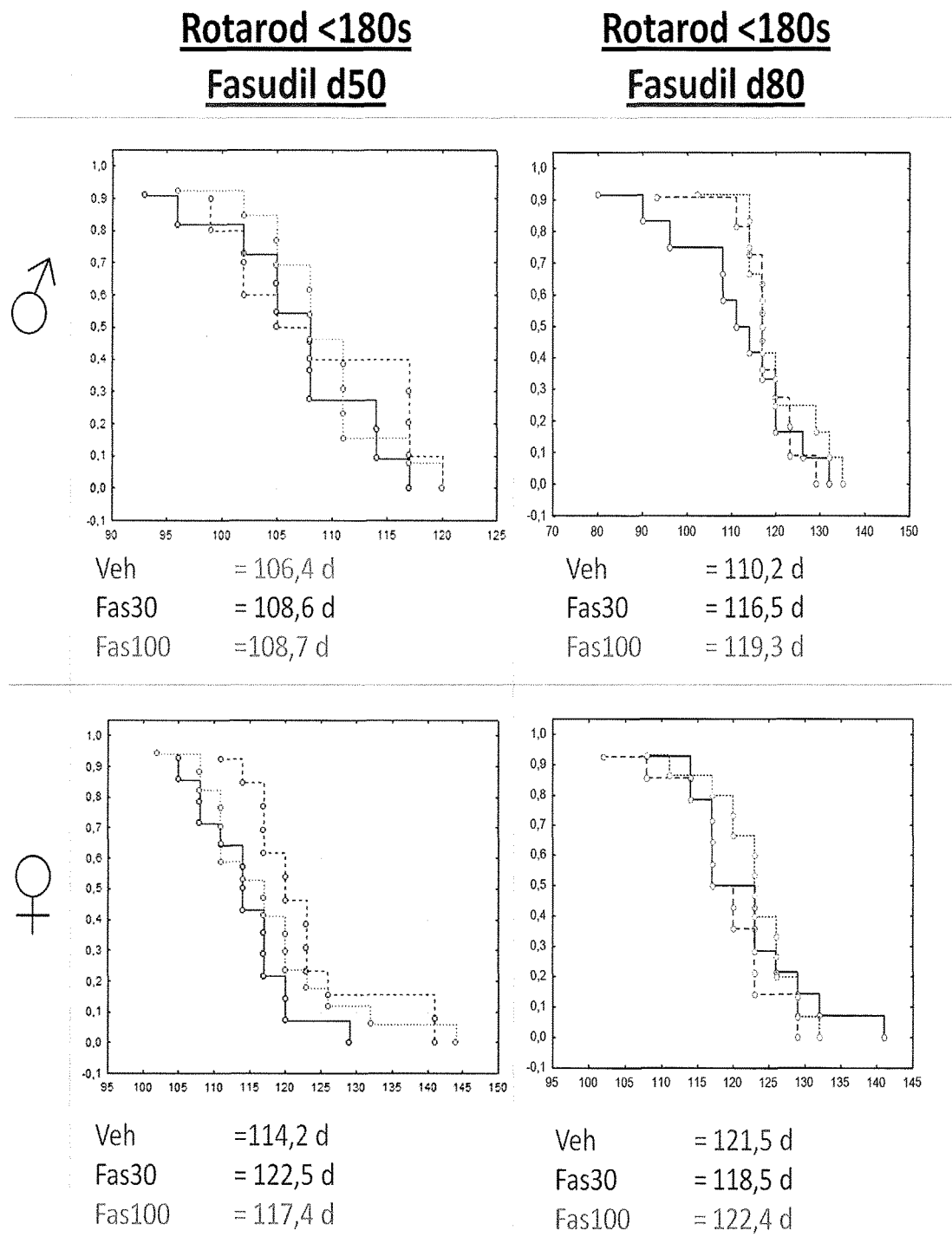
FIG. 5: Kaplan-Meier time-to-failure plot for 180 s rotarod performance in pre- and symptomatically treated male and female SOD1$^{G93A}$ mice. VEH: solid line; Fas30: dashed line; Fas100: pointed line.

Evaluating motor coordination by subjecting the animals to the rotarod test, the presymptomatic female treatment group failed later in the task to reach a total running time of 180 s (122.5 days) in comparison to the vehicle-treated group (114.2 days). For males, there was only a slight non-significant trend to improved performance in the presymptomatic Fas30 Group (FIG. 5). Wildtype animals always reached the maximum time of 180 s (data not shown).

Presymptomatically treated mice showed a prolonged time to the first failure in the rotarod test. This effect was most pronounced for female mice and moderately improved in male mice. A symptomatic treatment was not able to improve rotarod performances.

The hanging wire test evaluates crude grip strength of the upper extremities. It does not allow differentiating between only minor deficits in strength because the body weight of the animals is in relation to the grip strength relatively heavy.

Figure 6:
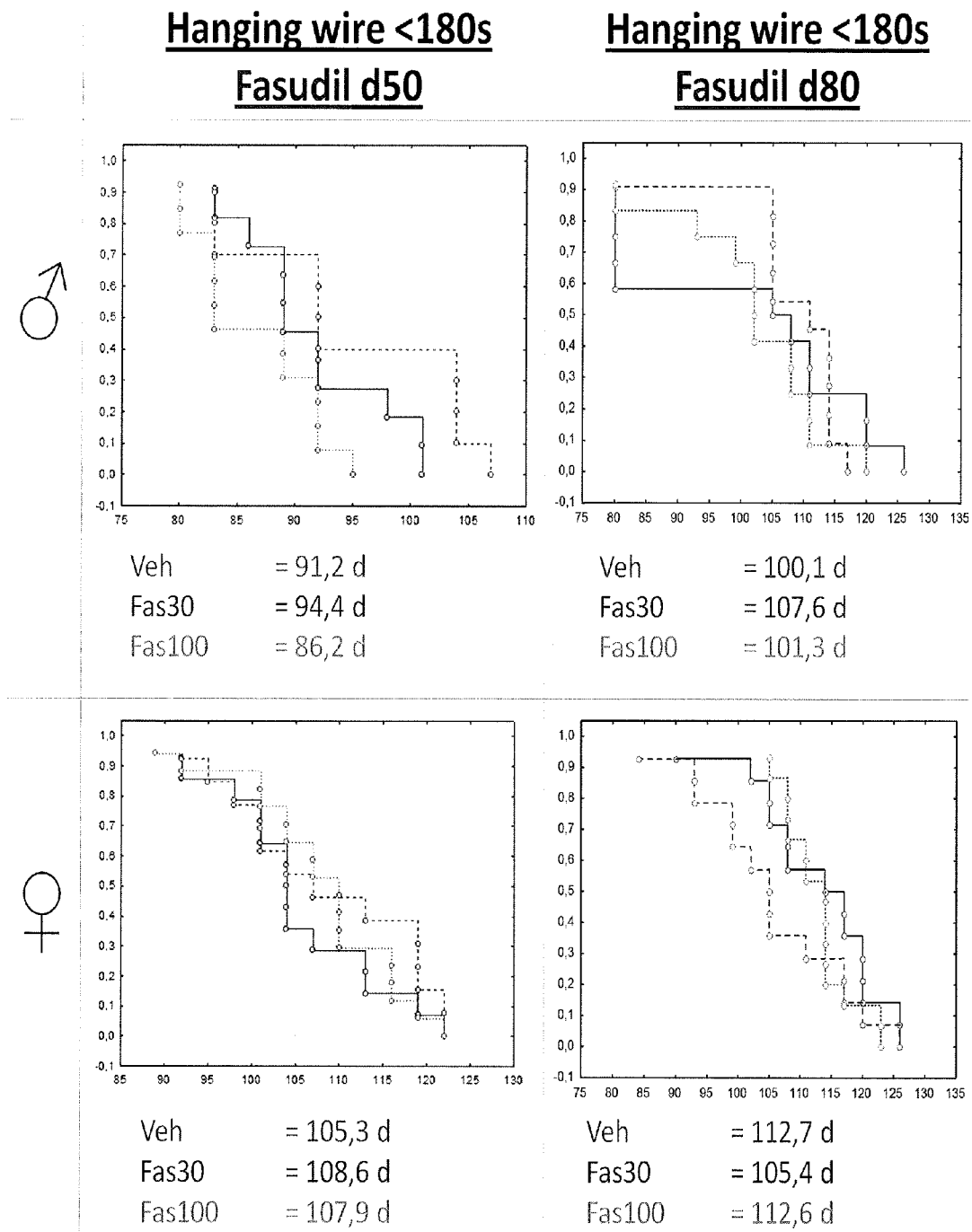
FIG. 6: Kaplan-Meier time-to-failure plot for 180 s hanging wire performance in pre- and symptomatically treated male and female SOD1$^{G93A}$ mice. VEH: solid line; Fas30: dashed line; Fas100: pointed line.

The hanging wire performance evaluating crude muscular strength in the task to reach a total hanging wire time of 180 s was not different in either treatment groups of both sexes (FIG. 6). Wildtype animals always reached the maximum time of 180 s (data not shown).

In both presymptomatic and symptomatic treatment groups the time to failure in this test was prolonged only to a very moderate but not significant amount in comparison to controls. Thus Fasudil seems to rather improve fine motor coordination than crude muscular strength.

Motoneurons of Female SOD G93A Mice are Protected by Presymptomatic Fasudil Treatment In order to correlate the clinical and behavioural results to the neurodegenerative disease process on a histological level the inventors chose to evaluate first the survival of spinal cord motoneurons and second of spinal cord astrogliosis. The analysis of ChAT positive motoneurons in the spinal cord represents a basic marker of ALS pathology, however, does not necessarily reflect the functional integrity of this principal part of the motor unit. Whereas the inventors had undertaken the clinical and behavioural testings repeatedly during the entire disease process the inventors were confined to one time point of each experimental group to perform the immunohistochemical analysis after sacrification of the animal. As clinical disease is already very obvious at d100 the inventors chose this time point for analysis and additionally examined all animals at time of death.

Figure 3:
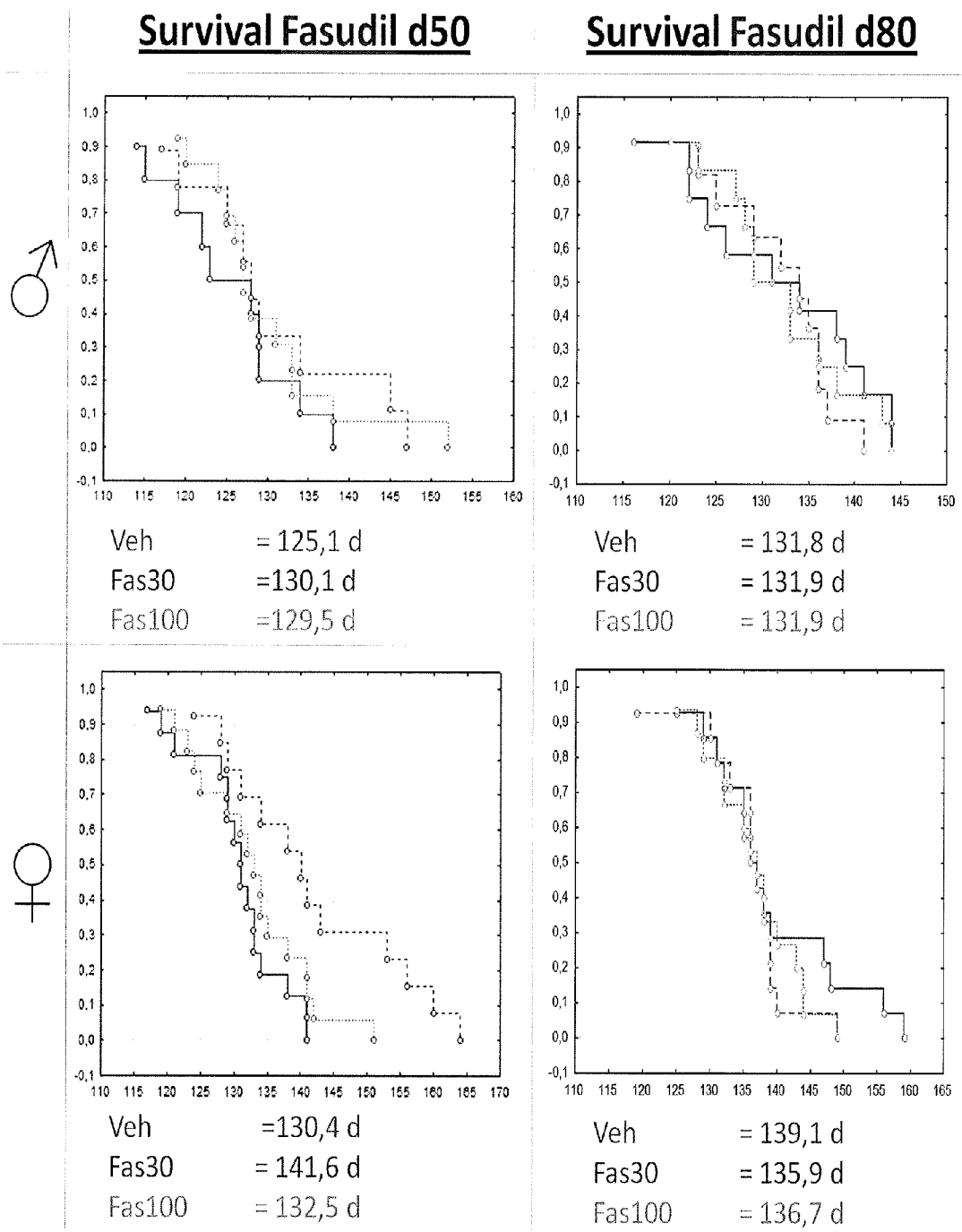
FIG. 3: Kaplan-Meier survival plot for age at death in pre- and symptomatically treated male and female SOD1$^{G93A}$ mice. VEH: solid line; Fas30: dashed line; Fas100: pointed line.
Figure 4:
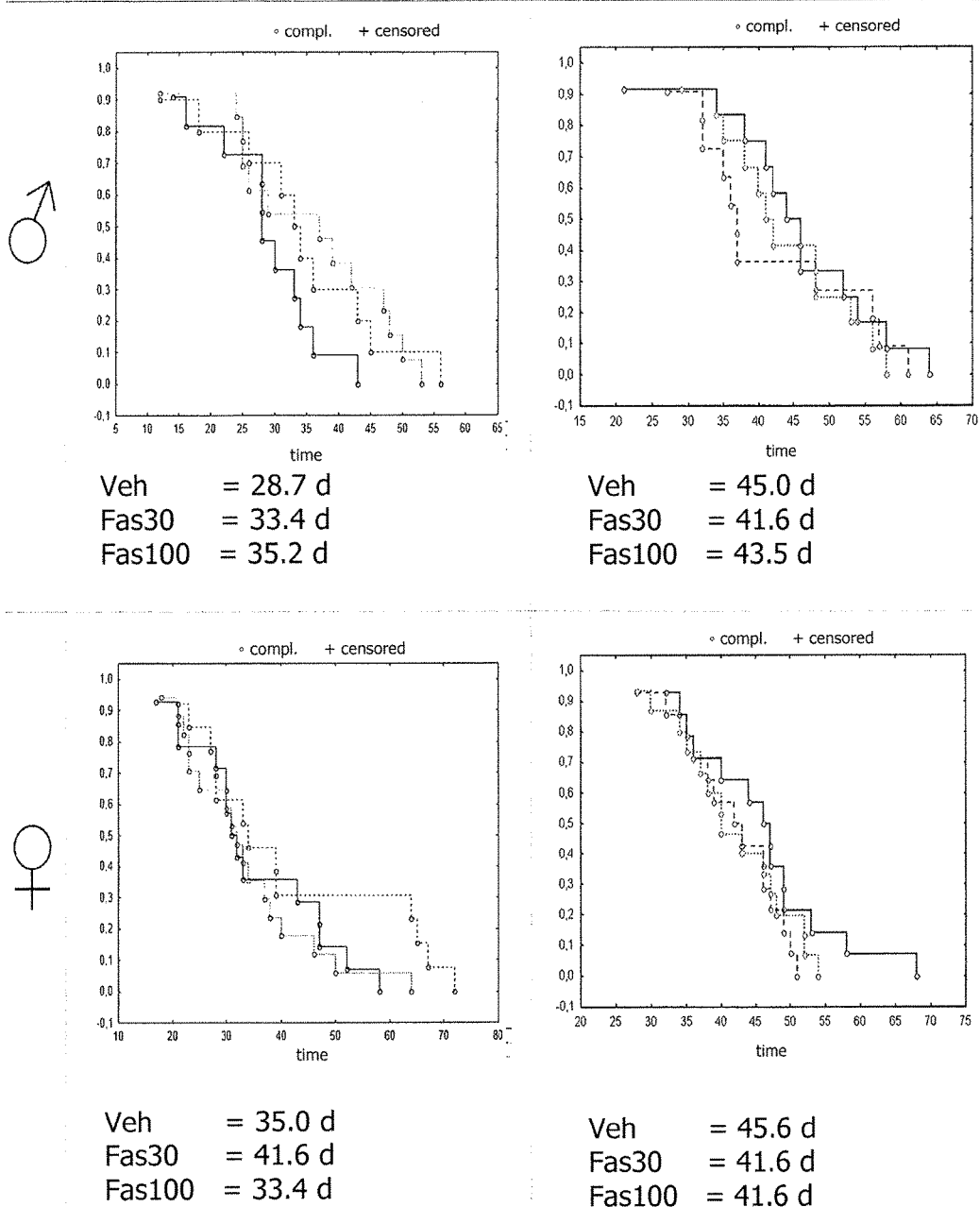
FIG. 4: Disease duration for pre- and symptomatically treated male and female SOD 1$^{G93A}$ mice. VEH: solid line; Fas30: dashed line; Fas100: pointed line.

Motor function is dependent on the number of functional motor units that are comprised of the motoneuron, its axon, the neuromuscular junction and the innervated muscle fibers. As the number of motoneuron cell bodies is a critical component of these motor units and ROCK inhibition has shown to be able to confer a cytoprotective effect on neuronal cells the inventors compared the numbers of ChAT positive motoneurons between treatment groups. Therefore, the inventors analyzed motoneuron numbers of treated animals at day 100 of life and at time of death which can however be different for the individual animal (compare FIG. 3).

Figure 7:
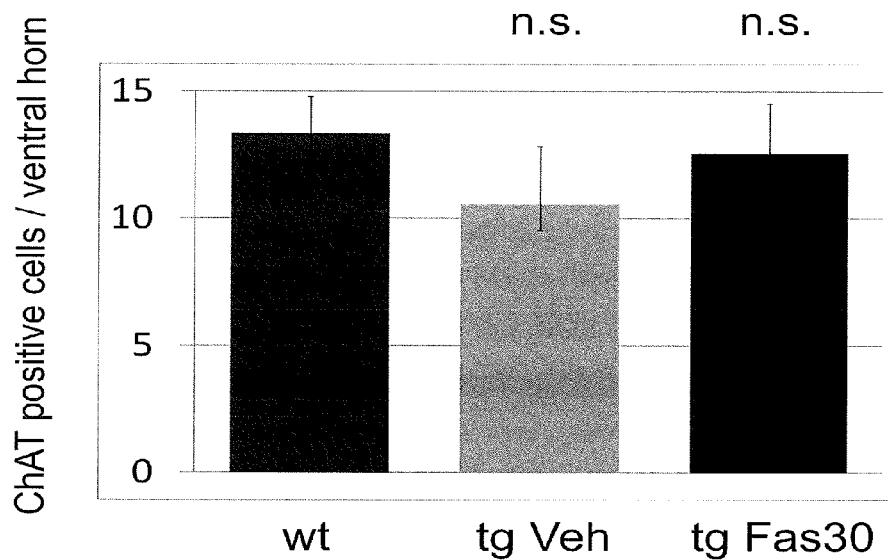
FIG. 7: Average count of ChAT positive motoneurons per lumbar spinal cord section for presymptomatically treated male and female SOD1$^{G93A}$ mice at day 100.

The motoneuron analysis performed at day 100 for presymptomatically treated female mice showed only a minor loss of motoneuron numbers between wildtype and transgenic vehicle treated mice. Obviously, the loss of motoneurons is only moderate at that early time point of clinical disease. If transgenic animals were compared that received either vehicle or Fas30, the latter ones showed a strong trend of elevated numbers of motoneurons (FIG. 7).

Figure 8:
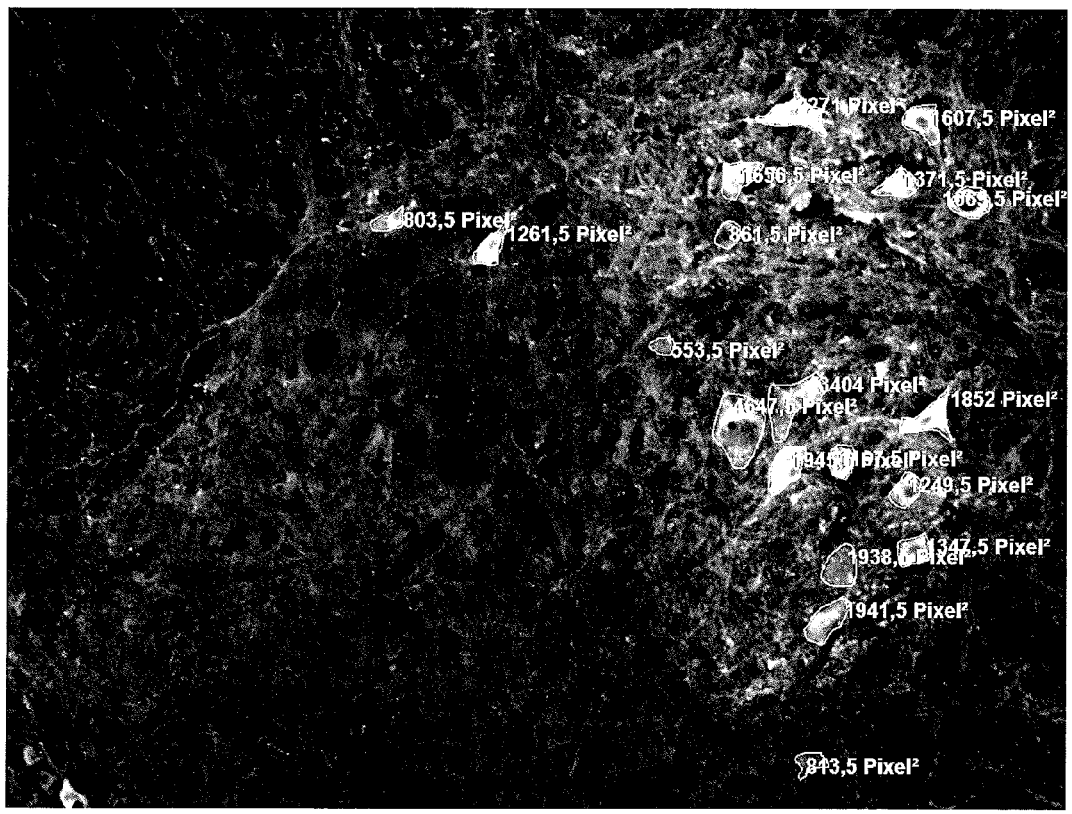
FIG. 8: Example of size measurement of ChAT positive motoneuron cell body area per lumbar spinal cord section in female SOD1$^{G93A}$ mice at day 100.

Because motoneurons exhibit large motoneuron cell bodies and it is generally acknowledged that the size of the cell body can also be seen as a marker for intact cell viability, the inventors measured the sizes of all motoneurons in the different animal groups (example in FIG. 8).

Figure 9:
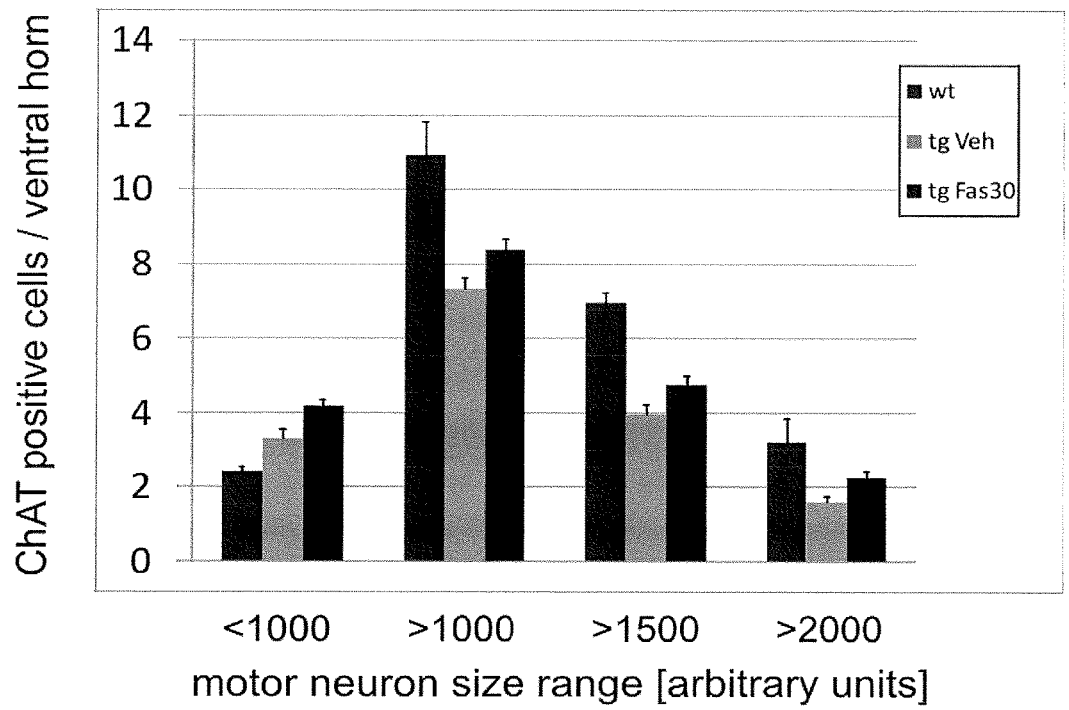
FIG. 9: Differentiation of ChAT positive motoneurons by size range in female SOD1$^{G93A}$ mice at day 100. From left to right each size range: wt; tg Veh; tg Fas30.

If the absolute numbers of motoneurons were differentiated by cell body size transgenic animals had lesser motoneurons in all size groups. Although the transgenic Fas30 group displayed more motoneurons in all size groups, this trend was not significant (FIG. 9).

Figure 10:
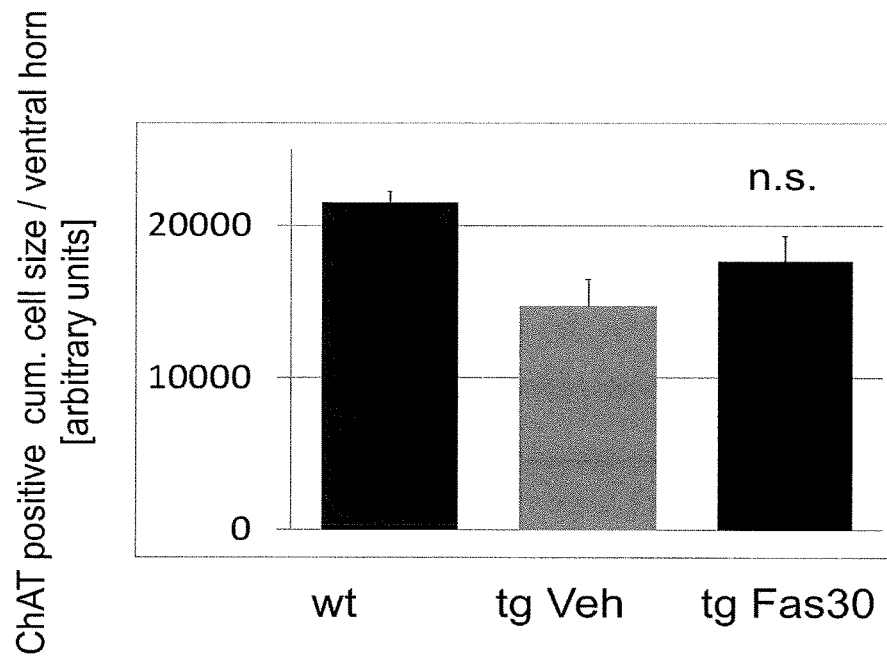
FIG. 10: Cumulative cell size per ventral horn section in female SOD1$^{G93A}$ mice at day 100.

If cumulative values of the cell body size per anterior horn section were compared between groups, the cumulative size in the transgenic Fasudil group showed a defined trend to be larger than the vehicle treated group (FIG. 10).

Figure 11A:
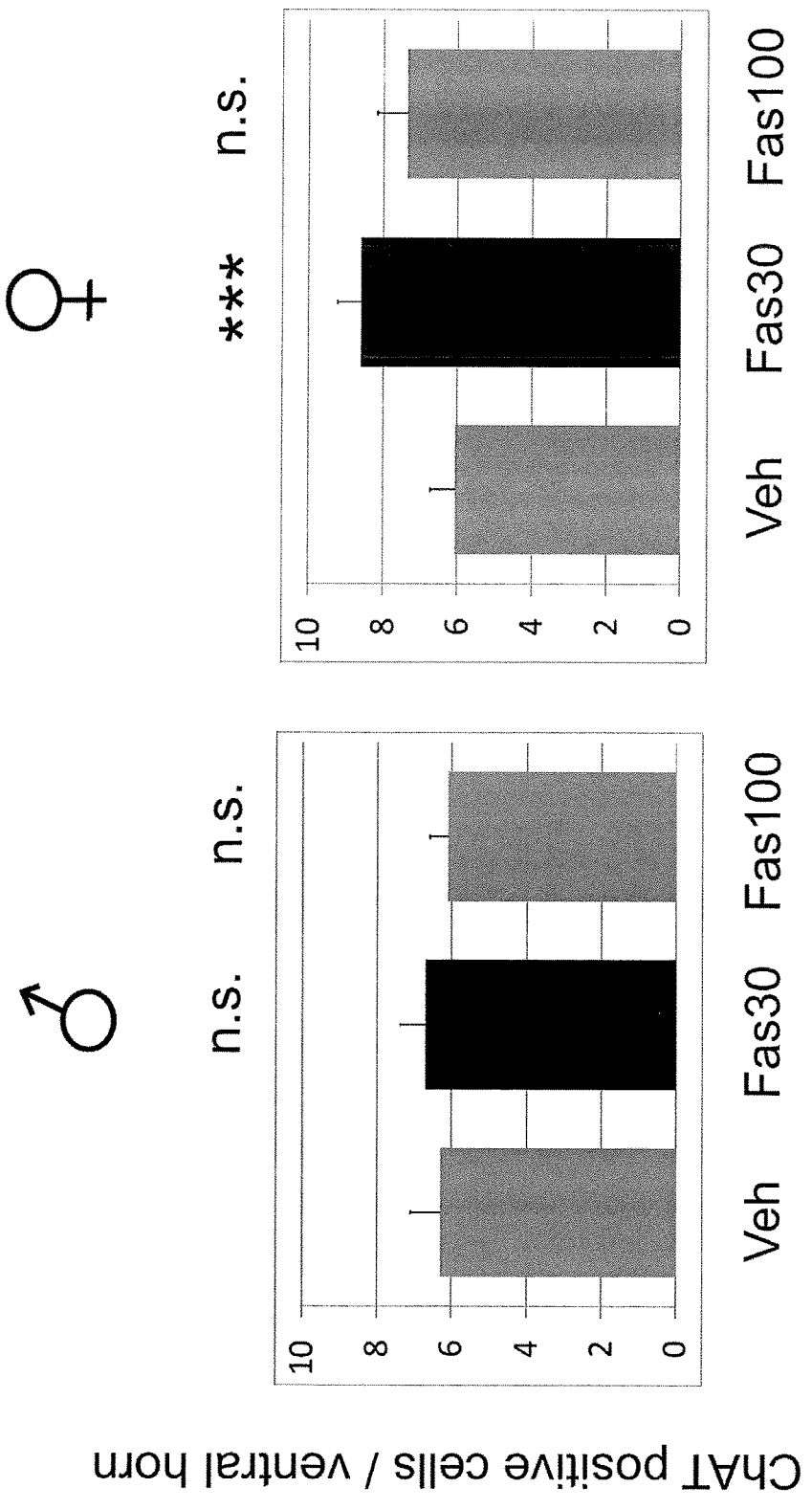
FIG. 11: (a): Average count of ChAT positive motoneurons per lumbar spinal cord section for presymptomatically treated male and female SOD1$^{G93A}$ mice at time of death. (b): Average count of ChAT positive motoneurons per lumbar spinal cord section for presymptomatically and symptomatically treated male and female SOD1$^{G93A}$ mice at time of death. From left to right: Veh; Fas30; Fas100.
Figure 11B:
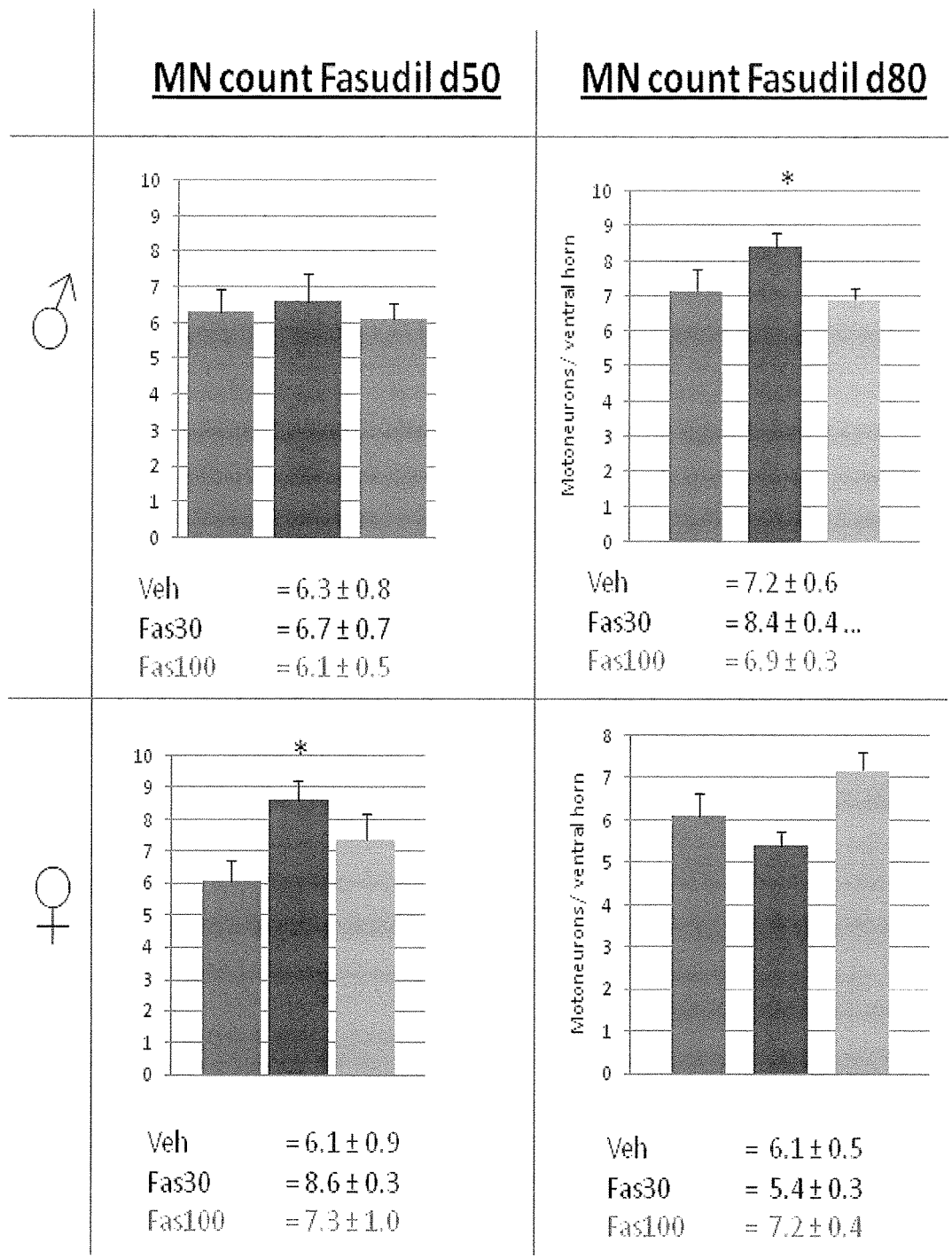

Whereas motoneuron cell numbers were not significantly altered in both transgenic treatment groups at day 100, the presymptomatically treated animals analyzed at time of death showed significant differences. In contrast to the low number of ChAT cell numbers per lumbar spinal cord section in vehicle treated female mice (6.1±0.95), female Fas30 treated animals had a significantly increased motoneuron count (8.6±0.36) that was not found in the high dose F100 group (7.3±1.00). The presymptomatic male groups did not profit from either Fas30 or Fas100 treatment (FIG. 11a). However, the symptomatic male treatment group exhibited higher motoneuron numbers with Fas30 treatment than the vehicle group. The female symptomatic treatment groups did not differ regarding motoneuron cell counts (overview of all data in FIG. 11b).

Presymptomatically Fasudil treated mice showed a trend of increased numbers of spinal cord motoneurons at day 100, however, that was not significant as also in comparison to wildtype animals most motoneurons were not yet severely affected by the disease process. The analysis at time of death resulted in increased motoneurons numbers for female mice. The symptomatic treatment was not able to improve motoneuron survival.

Astrocytosis is Reduced in Presymptomatically Treated Fasudil Mice

Figure 12:
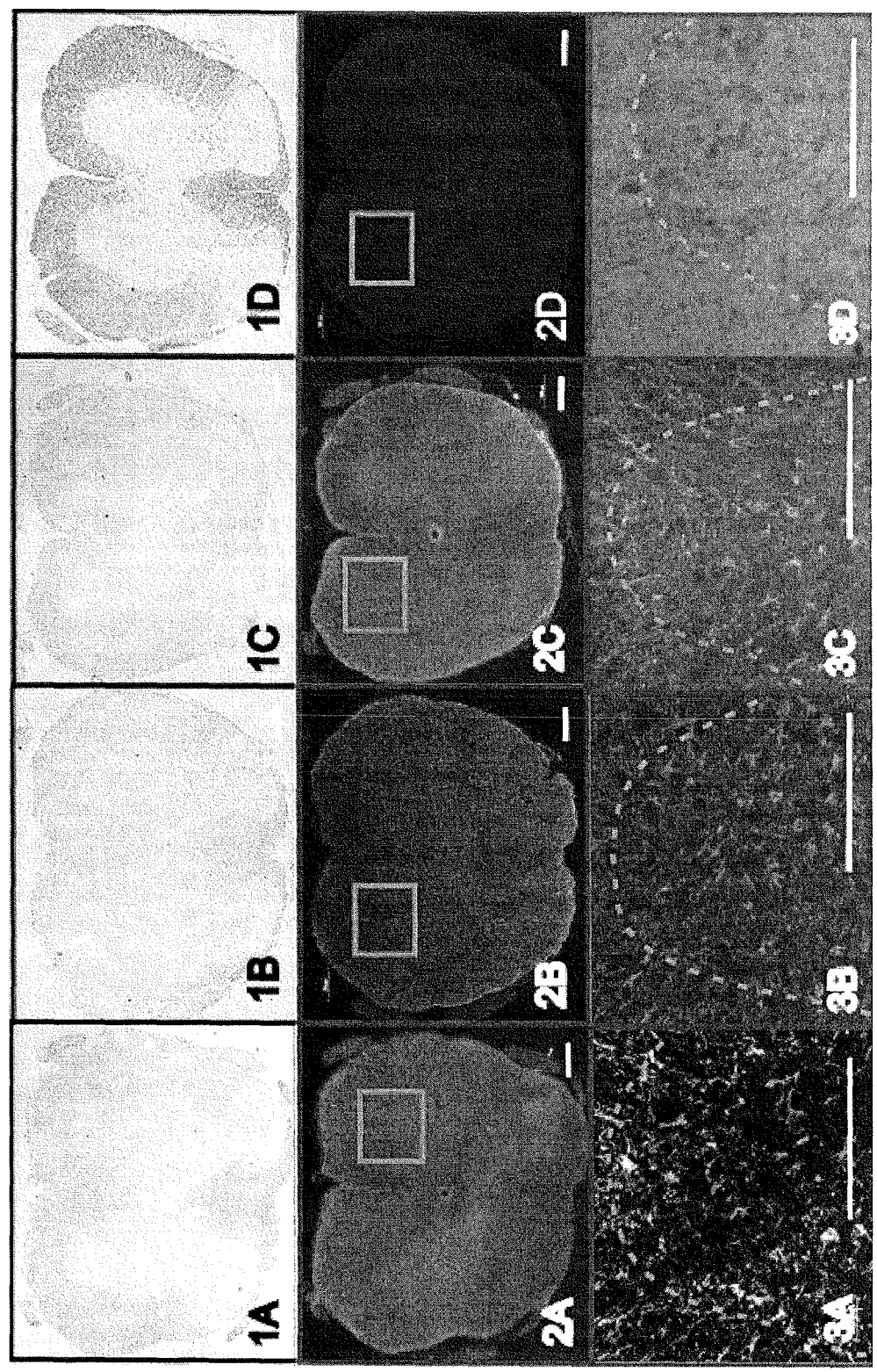
FIG. 12: Astrocytosis in SOD G93A transgenic mice treated with Vehicle control (1A-3A), Fas30 (1B-3B) or Fas100 (1C-3C), immunohistochemical (IHC) labeling control without primary antibody (1D-3D). 1A-D: Spinal cord axial sections in phase contrast (overview). 2A-D Spinal cord axial sections labeled with GFAP/Cy2 (overview). The corresponding insets of the ventral horn are displayed in a higher magnification in 3A-D, dashed lines mark the border of the ventral horn. Scale bar in 2 and 3 is 200 µm.

Reactive astrogliosis represents another parameter in the evaluation of histologic manifestation of ALS disease. In human ALS patients, the clinical progression of this neurodegenerative disease seems to be associated with changes in astrocytic cell infiltration in the spinal cord. Therefore, the inventors evaluated the extent of astrogliosis in the lumbar spinal cord by counting the number of GFAP positive astroglial cells in the ventral horn and normalized values to area (FIG. 12).

Figure 13:
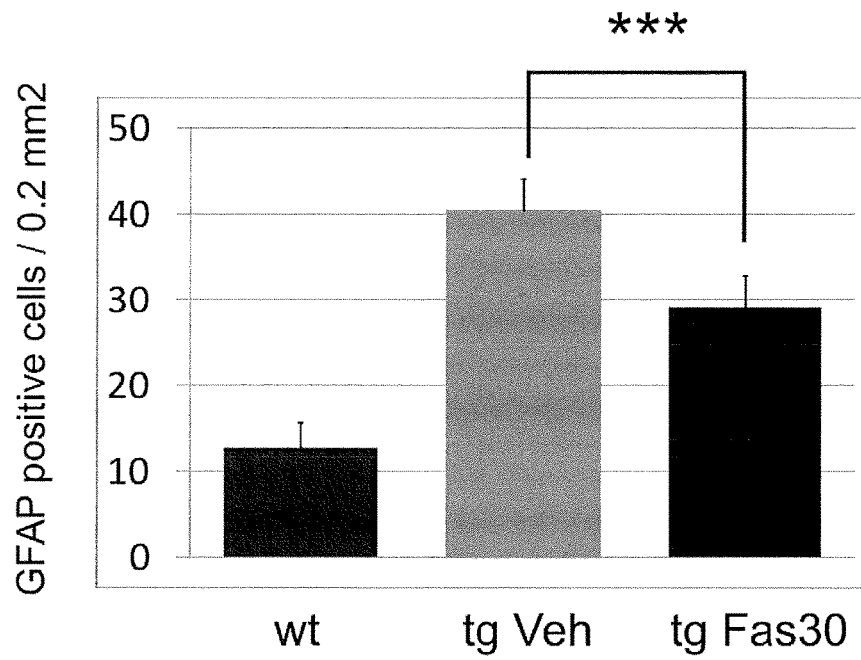
FIG. 13: GFAP positive astrocytes per 0.2 mm$^2$ in the anterior horn of lumbar spinal cord in wt and presymptomatically treated tg female SOD1$^{G93A}$ mice at day 100.

Comparable to the analysis of surviving motoneurons the inventors evaluated animals at day 100 of life and at time of death. Astroglial cell numbers at day 100 in female mice between wildtype and transgenic animals were significantly higher in the transgenic vehicle group. In comparison to the transgenic vehicle treated animals Fas30 significantly reduced the GFAP cell number (FIG. 13).

Figure 14:
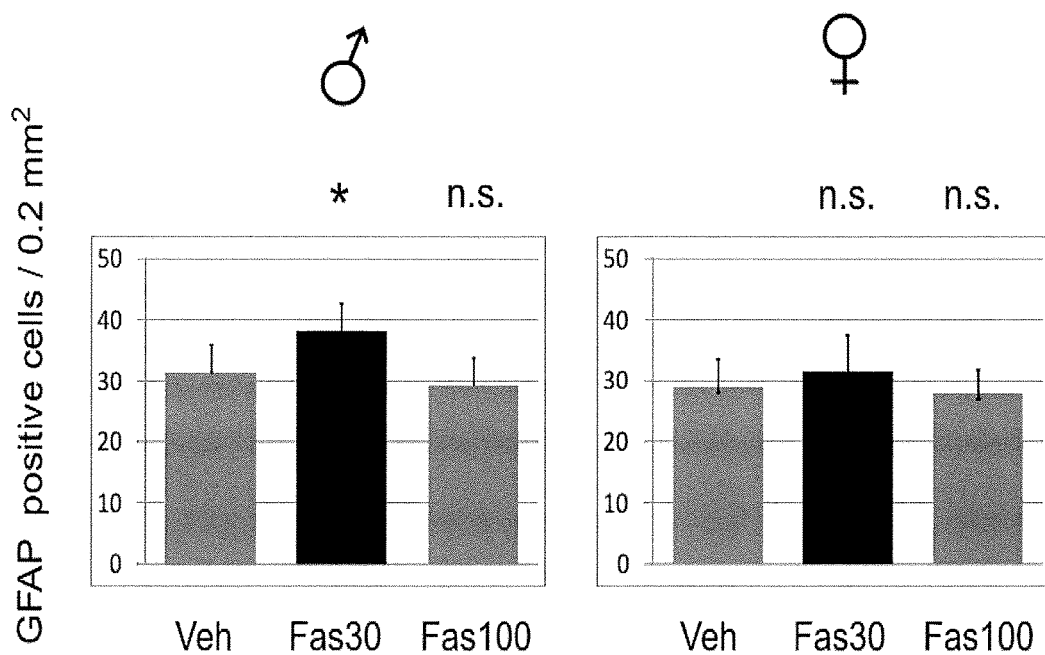
FIG. 14: Numbers of GFAP positive astrocytes per 0.2 mm$^2$ of ventral horn of lumbar spinal cord in SOD1$^{G93A}$ mice.

The quantitative analysis of presymptomatically treated mice at time point of death resulted in lower numbers of astrocytes in vehicle treated transgenic animals compared to day 100. Comparing the treatment groups of transgenic animals, numbers of GFAP positive astroglia were slightly higher for the Fas30 male (38.2±4.4) but not for the Fas30 female (31.6±5.9) group. The Fas100 groups (male 29.24±4.5; female 27.9±4.0) did not differ from vehicle controls (male 31.3±4.7; female 28.91±4.7) (FIG. 14).

By evaluating numbers of GFAP positive astroglia in the spinal cord the presymptomatically treated female animals had significantly less infiltrating astroglia reflecting that this reactive astrogliosis had not as far evolved as in the untreated mice. The ability of Fasudil to influence inflammatory processes has also been demonstrated by other groups. The analysis of presymptomatically treated mice at time of death resulted in an unexpected finding. Here, both male and female mice showed higher numbers of astroglia. The inventors attribute this finding to the prolonged life time of the animals and speculate that whereas at the same time points like day 100 animals exhibit less astrogliosis with Fasudil treatment they have a strong "extra" accumulation until end stage/time of death that is on average more than one week later than in vehicle treated animals. It seems like a "bursting of a dam" takes place and leads to an exponential astroglia infiltration in this very late clinical stage. Interestingly, the prolonged time of life did not negatively influence motoneuron numbers that rather seem to be more stably conserved from early time points on.

Moreover, motor function is dependent on the number of functional motor units that are comprised not only of the spinal cord motoneuron itself, but also of its axon, the neuromuscular junction and the innervated muscle fibers. Therefore, the inventors did not only investigate spinal cord ALS pathology but also the remaining distal compartments of the PNS and innervated muscle.

However, evaluating sciatic nerve axonal pathology and NMJ integrity of gastrocnemius muscle, there were no significant differences between Fasudil and control treated animals.

In a corresponding in vitro paradigm of motoneuron survival, Fasudil robustly protected motoneurons from cell death in a co-culture with astrocytes but also in mono-culture.

Axonal Degeneration is not Altered after Fasudil Treatment

Figure 15:
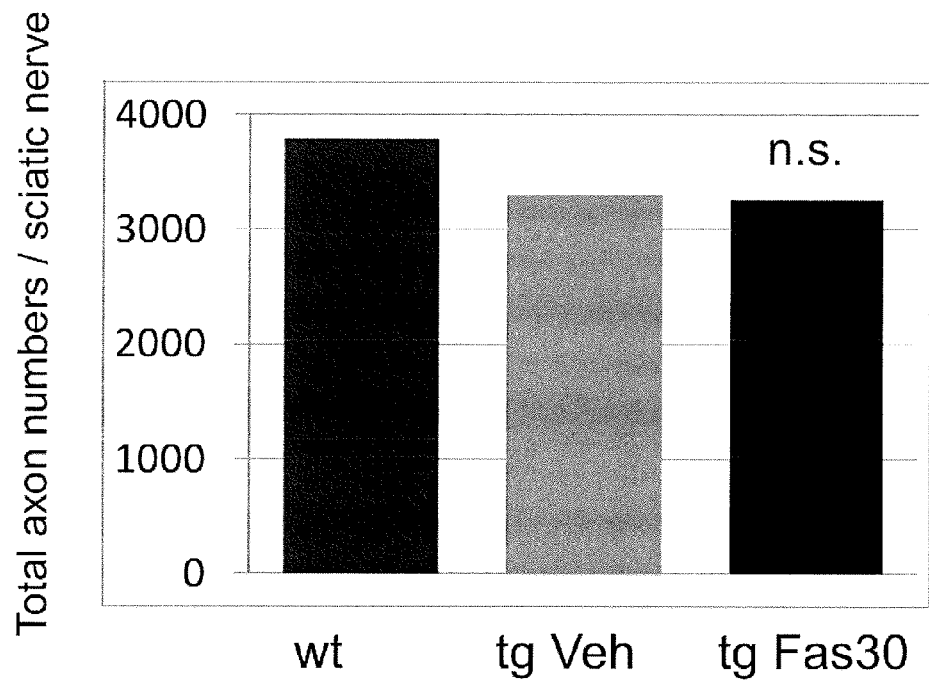
FIG. 15: Total axon numbers in the sciatic nerve of female SOD1$^{G93A}$ mice at day 100.

The degeneration of motor axons is an early event in the development of ALS disease that has important functional consequences. Therefore, the inventors analyzed the extent of axonal degeneration in the sciatic nerve in wildtype and ALS mice at day 100 in females. The manual counting of the total number of preserved axons in the sciatic nerve resulted in a significantly decreased axonal number in transgenic animals in comparison to wildtype animals. The transgenic vehicle group and the Fas30 group showed comparable axon numbers (FIG. 15).

Figure 16:
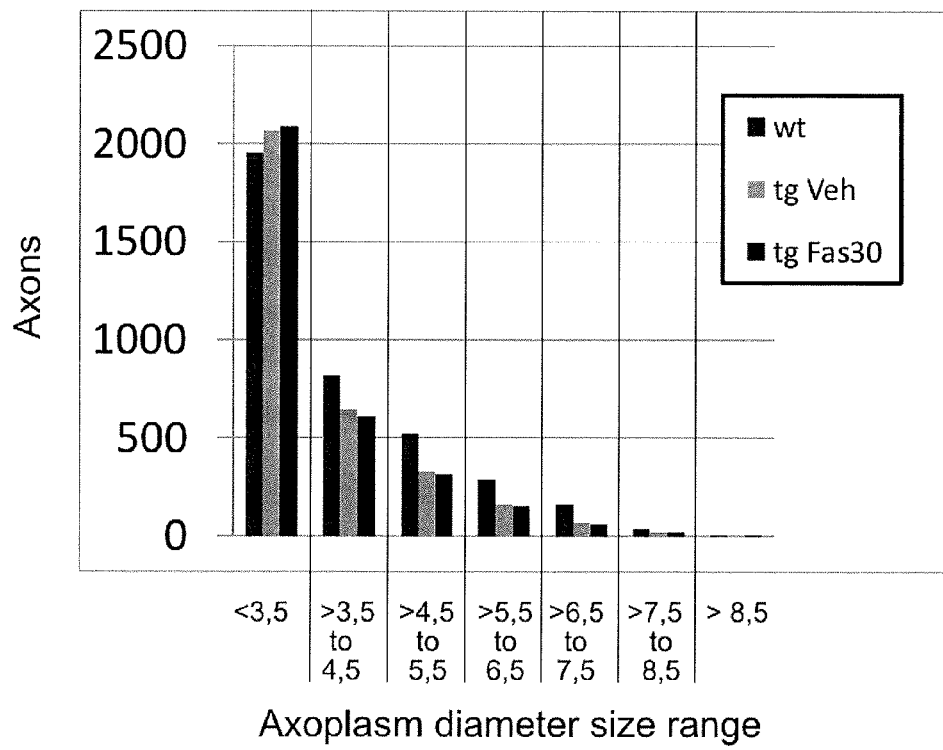
FIG. 16: Axon numbers in the sciatic nerve of female SOD1$^{G93A}$ mice at day 100 differentiated by size range. From left to right each size range: wt; tg Veh; tg Fas30.

If differentiated by axoplasmal diameter size range, the axonal number in each size range was higher in wildtype than in transgenic animals except for the size range smaller than 3.5 µm. There were no significant differences between transgenic vehicle treated and Fas30 treated animals (FIG. 16).

Comparative Example

If SOD G93A mice were treated with the pharmacologically more potent ROCK inhibitor Y-27632 (10 mg/kg body weight) in a presymptomatic treatment paradigm from d50 on, there were no significant effects seen concerning survival (cf. FIG. 19).

Example 2

Fasudil Protects Cultured Motoneurons from Kainic Acid Toxicity

Figure 17:
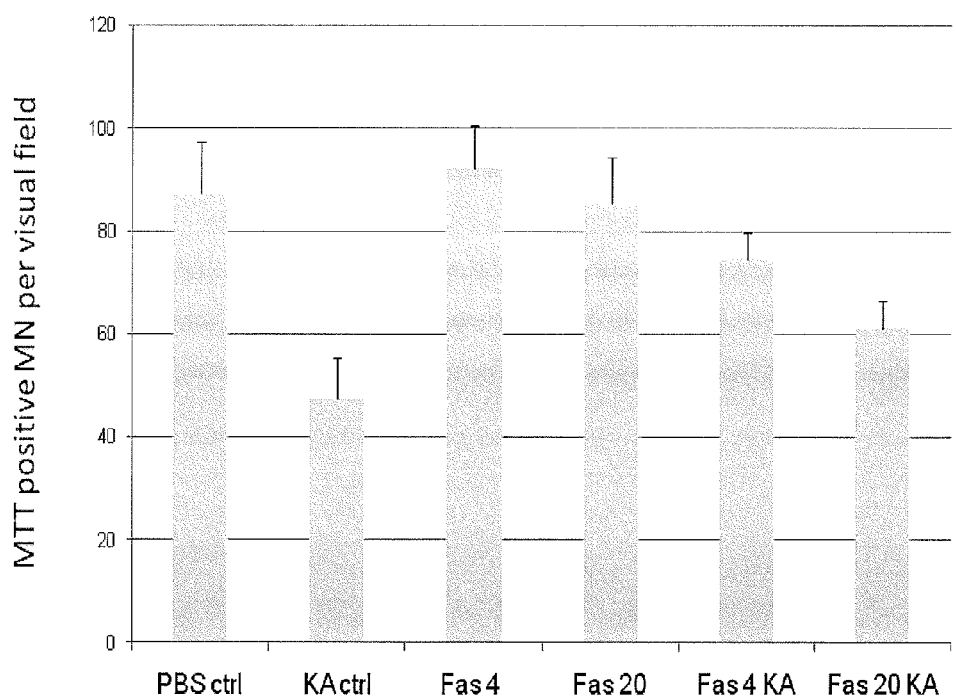
FIG. 17: Survival of KA exposed motoneurons in astrocyte-motoneuron co-cultures of control and Fasudil treated conditions.

In order to compare the Fasudil neuroprotective effect on motoneurons in vivo with an corresponding in vitro paradigm the inventors subjected wildtype primary motoneurons cultured in a astrocyte/motoneuron co-culture to kainic acid (KA) toxicity. KA exposure for 24 h dramatically decreased the number of viable motoneurons. However, if cultures had been treated with Fasudil at 4 or 20 µM concentration, the reduction in viable motoneurons declined significantly less. Thus Fasudil protected motoneurons from KA induced cell death (FIG. 17).

Figure 18:
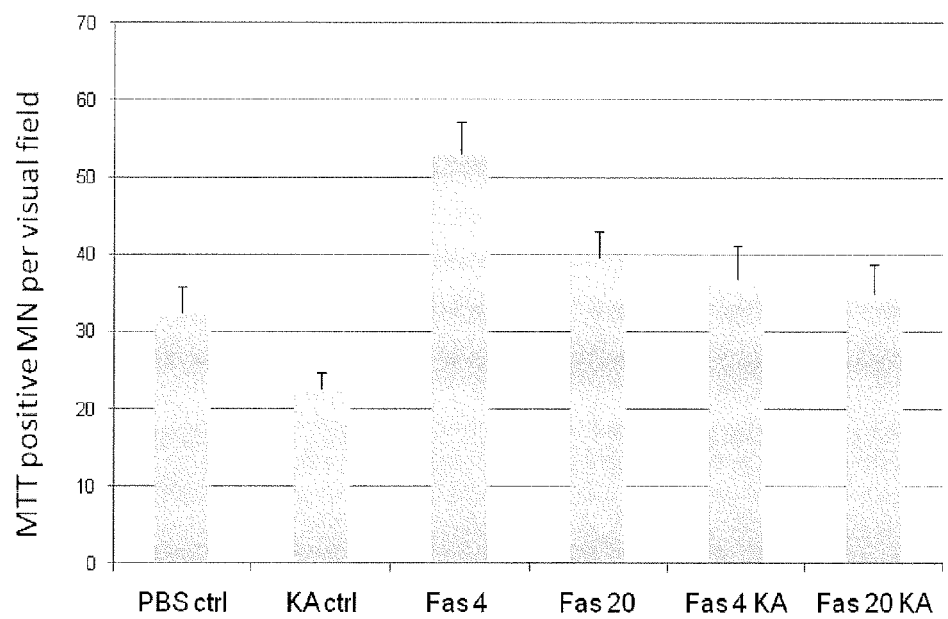
FIG. 18: Survival of KA exposed motoneurons in monoculture of control and Fasudil treated conditions.

Fasudil was also effectively protecting mono-cultures of primary motoneurons thus indicating that the protective effect does not depend on co-cultured astrocytes (FIG. 18).

In summary, Fasudil protected motoneurons from cell death in a co-culture with astrocytes but also in mono-culture in a corresponding in vitro paradigm of motoneuron survival.

Example 3

Materials and Methods

Microglial Cell Preparation, Culturing and Treatment

Primary cell cultures were prepared from whole brains of newborn (P0) mice and cultured in complete Dulbecco's modified Eagle's medium (DMEM, Invitrogen/Gibco, Karlsruhe, Germany), supplemented with 10% fetal calf serum (FCS, Invitrogen/Gibco), 100 U/ml penicillin and 100 µg/ml streptomycin (both Biochrom, Berlin, Germany) as previously described (Regen, et al. (2011) Brain, Behavior, and Immunity 25(5): 957-970). In brief, brains of newborn B6/SJL SOD1G93A and from B6/SJL SOD1wt, respectively, were liberated from meninges and blood vessels, washed with Hank's balanced salt solution (HBSS; Biochrom) and incubated with 2.5% trypsin (Biochrom) for 10 min at 37° C. The enzymatic reaction was stopped by addition of complete medium, supplemented with DNAse [5 mg/ml] (Worthington Biochemicals, Lakewood, N.J., USA). Remaining cell clusters were mechanically separated and the suspension was centrifuged at 900 rpm at 4° C. for 10 min. The supernatant was removed, cells were resuspended in fresh complete medium and seeded in 75 cm2, poly-L-lysine (PLL)-coated culture flasks. Immediately before being used, flasks were incubated with 100 µg/ml PLL (Invitrogen/Gibco) for 30 min at RT and excess of PLL was washed off by three rinses with sterile ddH2O. Subsequently, cultures were maintained in a humidified atmosphere with 5% $CO_2$ at 37° C. On the next day, primary mixed-glial cultures were washed three times (PBS, Invitrogen/Gibco) and received fresh complete medium, the latter being repeated the following day. One week after seeding, microglial proliferation was stimulated by adding complete medium supplemented with 30% of L929-conditioned cell culture supernatant (see section "L929 Mouse Fibroblast Cultures" below). After another two days, microglial cells were harvested by shaking them off the astrocytic layer, taking advantage of their different adhesion properties. After washing with complete medium and counting, cells were plated in 96-well plates at a density of 15,000 cells/well for ELISA or were plated in 24-well plates at a density of 50,000 cells/well on PLL-coated coverslips for later immunocytochemical processing. The purity of the microglial preparations was routinely >98%, based on nuclear staining with DAPI, immunocytochemistry for CD11b and Iba1 as well as Griffonia simplicifolia isolectin B4-based labeling (data not shown).

Primary cultures underwent five different general treatments: (a) Cells were left untreated in medium serving as controls. (b) Cells were stimulated with the TLR4 ligand LPS (E. coli R515; Axxora/Appotech TLR ligand set 1, APO.54N-018) for 18 hours at a final concentration of 10 ng/ml. (c) Cells underwent a treatment with Fasudil at 2 µM, 10 µM or 50 µM, respectively, for 18 hours. (d) Cells were stimulated with LPS, as described above, in the presence of various concentrations of Fasudil. (e) Cells were preincubated for 1 h, 4 h or 12 h, respectively with Fasudil at 50 µM, prior to a LPS challenge in the continued presence of Fasudil at 50 µM. Stimulation experiments were routinely carried out twice.

Determination of Microglial Cell Vitality

Microglial viability was assayed as metabolic activity using WST-1 reagent (4-[3-(4-iodophenyl)-2-(4-nitrophenyl)-2H-5-tetrazolio]-1,3-benzene disulfonate), based on the enzymatic cleavage of WST tetrazolium salt to formazan by the succinate-tetrazolium reductase system of the respiratory chain of intact mitochondria. The assay was performed according to the instructions of the manufacturer (Roche Applied Science, Mannheim, Germany). After 3 h of incubation, the resulting color reaction was measured at 450 nm (with 655 nm as the reference wavelength) in a microplate reader (Bio-Rad, Munich, Germany). Accordingly, Fasudil was set to a maximum concentration of 50 µM, since up to this concentration, there was no reduction in metabolic activity observed.

L929 Mouse Fibroblast Cultures

L929 fibroblasts were routinely cultured in complete medium and passaged (1:5) every two weeks. After 14 days of continuing cultivation (no medium change in between), supernatants were isolated and stored at −20° C. until used for the stimulation of microglial proliferation. After 30 passages, fresh L929 cultures were established from a stock stored in liquid nitrogen.

Cyto- and Chemokine Measurements (ELISA)

Following microglial stimulations and treatments, culture supernatants were collected and stored at −20° C. until assayed. Supernatants were analyzed for the release of cyto- and chemokines by commercial enzyme-linked immunosorbent assay (ELISA) test systems. Levels of IL-6, CCL2 (monocyte chemoattractant protein, MCP-1), CCL3 (macrophage inflammatory protein, MIP-1α) and CCL5 (regulated upon activation normal T-cell expressed and presumably secreted, RANTES) and CXCL1 (Chemokine (C-X-C motif) ligand 1) were determined using DuoSet ELISA Development Kits (R&D Systems). TNFα (tumor necrosis factor α) was determined using MAXTM ELISA kit (Biolegend). Absorbance was measured at 450 nm (with a 540 nm reference wavelength) using a microplate reader (Bio-Rad).

Results

Protective Properties of Fasudil May be Due to Activated Microglia of the Neuroprotective M2 Phenotype Microglial activation is a neuropathological hallmark of ALS. Microglia can have very distinct and different phenotypic states, and, depending on the physiologic conditions, may exert either a toxic or protective effect on neurons. Microglia of the M1 phenotype (classically activated microglia) are cytotoxic due to the secretion of prinflammatory cytokines and reactive oxygen species. Microglia of the M2 phenotype (alternatively activated microglia) block proinflammatory responses and produce increased levels of neurotrophic factors and anti-inflammatory cytokines (for a review, see Henkel et al. 2009). Up to now, manipulating these microglial neuroprotective or neurotoxic effector functions and attributes remain elusive and poor understood.

The extent of microglial cell dissemination in the lumbar spinal cord was evaluated with a marker of activated microglia (Iba1) as described above under the heading "Quantitative evaluation of spinal cord motoneurons and astroglia, sciatic nerve axons and NMJ".

Figure 20:
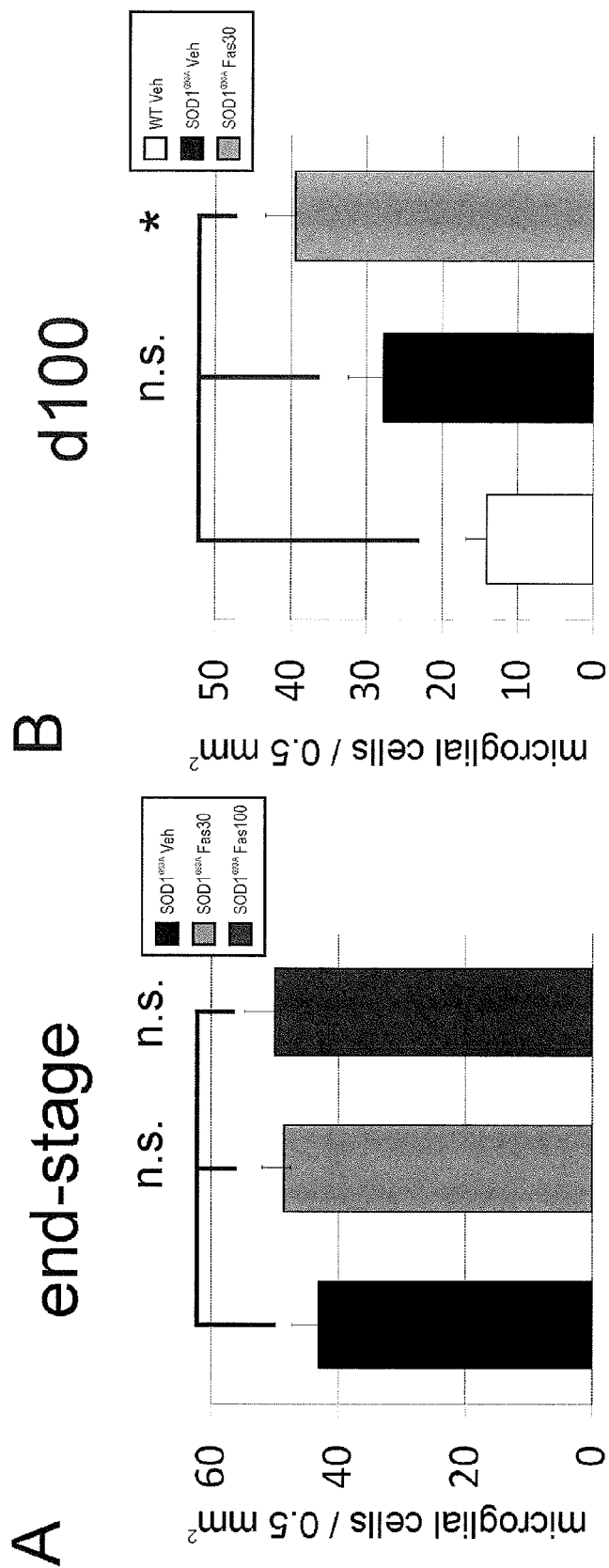
FIG. 20: Infiltration of Iba1 immunopositive microglial cells in the spinal cord anterior horn is modulated by ROCK inhibition. (A) Average number of Iba1 immunopositive microglia per 0.5 µm$^2$ in the spinal cord anterior horn in SOD1$^{G93A}$ mice treated with vehicle, Fas30 (Fasudil 30 mg/kg/d) or Fas100 (Fasudil 100 mg/kg/d) at disease end-stage. (B) Average number of Iba1 immunopositive microglia per 0.5 µm$^2$ in the spinal cord anterior horn in vehicle treated wildtype mice and in SOD1$^{G93A}$ mice treated with vehicle or Fas30 (Fasudil 30 mg/kg/d) at d100. (C,D) Representative images of immunofluorescent labelling of Iba1 positive microglia in spinal cord anterior horn at end-stage (C) or at d100 (D) (Iba1/Cy3 (red) and DAPI (blue)). Bar represents means±SEM. n.s. not significant; * $p<0.05$;  $p<0.01$; * $p<0.001$. Scale bars, 100 µm.
Figure 20:
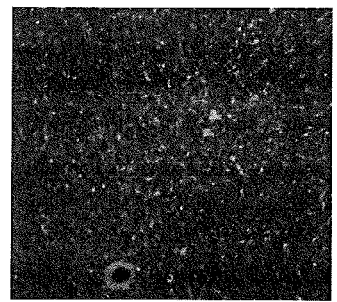
Figure 20:
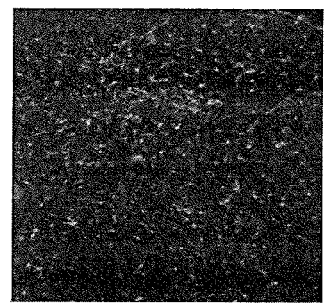
Figure 20:
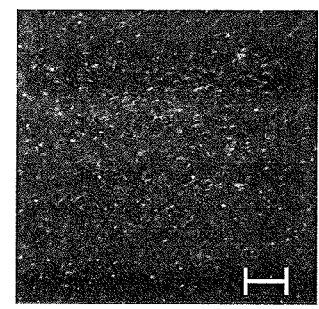
Figure 20:
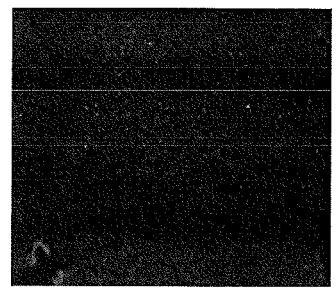
Figure 20:
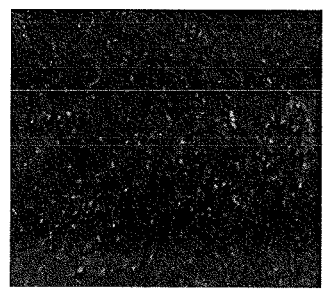
Figure 20:
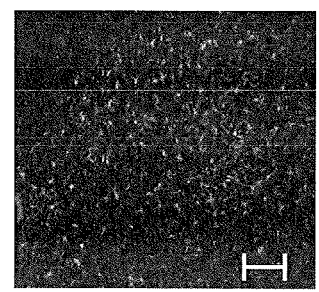

The results are shown in FIG. 20. Whereas there were no gross differences in the amount of microglial cells in all treatment groups at disease end-stage (vehicle group 43.2±4.2 cells/0.5 mm$^2$; Fas30 group 48.8±3.3 cells/0.5 mm$^2$; Fas100 group 50.2±4.7 cells/0.5 mm$^2$) (FIG. 20 A,C), the intermediate analysis during the disease course at d100 showed a significantly higher number of Iba1 immunopositive microglial cells in Fasudil 30 treated SOD1$^{G93A}$ mice (39.5±3.9 cells/0.5 mm$^2$) in comparison to vehicle treated SOD1$^{G93A}$ mice (27.8±4.7 cells/0.5 mm$^2$). Vehicle treated wildtype mice exhibited only very few spinal cord microglia (14.0±2.8 cells/0.5 mm$^2$) (FIG. 20 B,D).

The increased appearance of microglial cells in the Fasudil 30 treatment group at d100 could indicate a beneficial and neuroprotective M2 microglial response (cf. Henkel et al. 2009).

Figure 21:
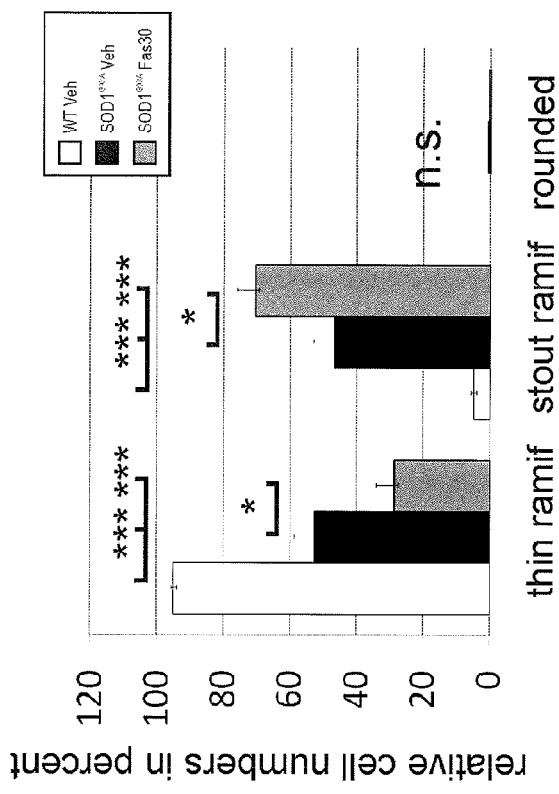
FIG. 21: Morphologic activatory changes of microglia in lumbar spinal cord after ROCK inhibition. (A) Quantitative analysis of relative cell numbers belonging to three different morphologic subtypes (thin ramified, stout ramified, rounded) of Iba1 immunopositive microglia in SOD1$^{G93A}$ mice treated with vehicle, Fas30 (Fasudil 30 mg/kg/d) or Fas100 (Fasudil 100 mg/kg/d) at end-stage. (B) Quantitative analysis of microglia morphology as in (A) for vehicle treated wildtype mice and SOD1$^{G93A}$ mice treated with vehicle or Fas30 (Fasudil 30 mg/kg/d) at d100. (C) Exemplary high magnification microscopic images of microglia morphologic types analyzed (Iba1/Cy3 (red) and DAPI (blue)). Bar represents means±SEM. n.s. not significant; * $p<0.05$; *** $p<0.001$. Scale bar, 50 µm.
Figure 21:
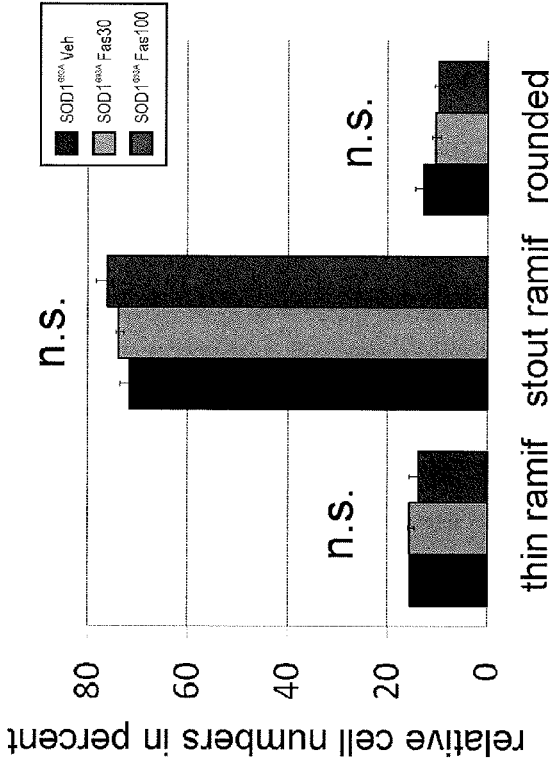
Figure 21:
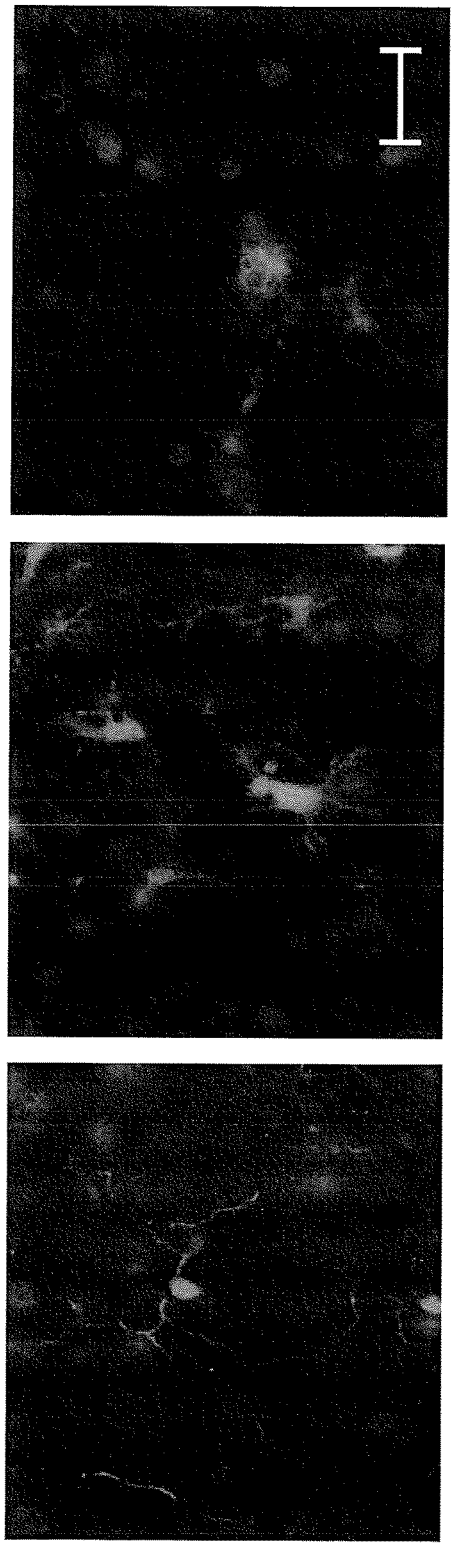

In order to further characterize the differential microglial behaviour in the treatment groups at d100, we performed a morphologic subclassification of microglial cells, as described above under the heading "Quantitative evaluation of spinal cord motoneurons and astroglia, sciatic nerve axons and NMJ". It is known that microglial morphology can be altered due to its activation state and cells may exhibit shapes with predominantly thin ramified processes, with predominantly stout ramified processes or with a round/amoeboid shape. The latter two morphologic cell types are considered to reflect a state of enhanced microglial activation in comparison to a surveillance type which is characterized by smaller cell bodies and thin ramified processes (exemplary microscopic images are shown in FIG. 21 C).

At disease end-stage there were no gross alterations of microglial morphology in all treatment groups. At this time point, the morphological type with stout ramified processes was mostly found (FIG. 21 A). However, at d100 microglia of Fasudil 30 treated SOD1$^{G93A}$ mice exhibited predominantly thin stout ramified processes (70.8±5.3%), less cells with thin ramifications (28.7±5.3%) and very few rounded cells (0.5±0.1%). In contrast, vehicle treated SOD1$^{G93A}$ mice had more cells with thin (52.6±6.3%) than with stout ramifications (46.7±6.3%) and very few rounded cells (0.7±0.2%). The vehicle treated wildtype group exhibited mostly thin ramified processes (95.0±0.8%), very few cells with stout ramifications (5.0±0.8%) and no rounded cells (0.0±0.0%) (FIG. 21 B).

Thus, it seems that an increased activation of microglial cells takes place, possibly exhibiting the neuroprotective M2 phenotype.

Figure 22:
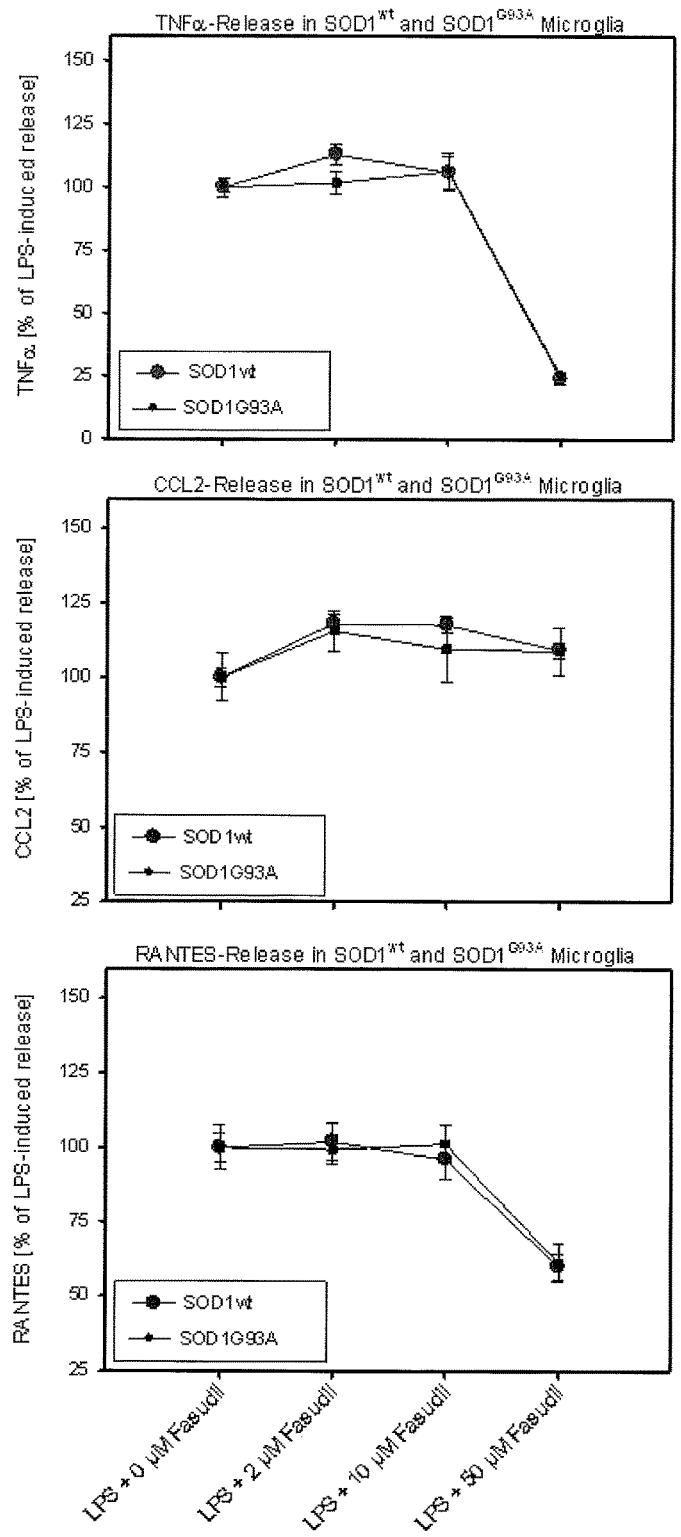
FIG. 22: Reduction of microglial cytokine/chemokine release by combined LPS+Fasudil treatment.
Figure 22:
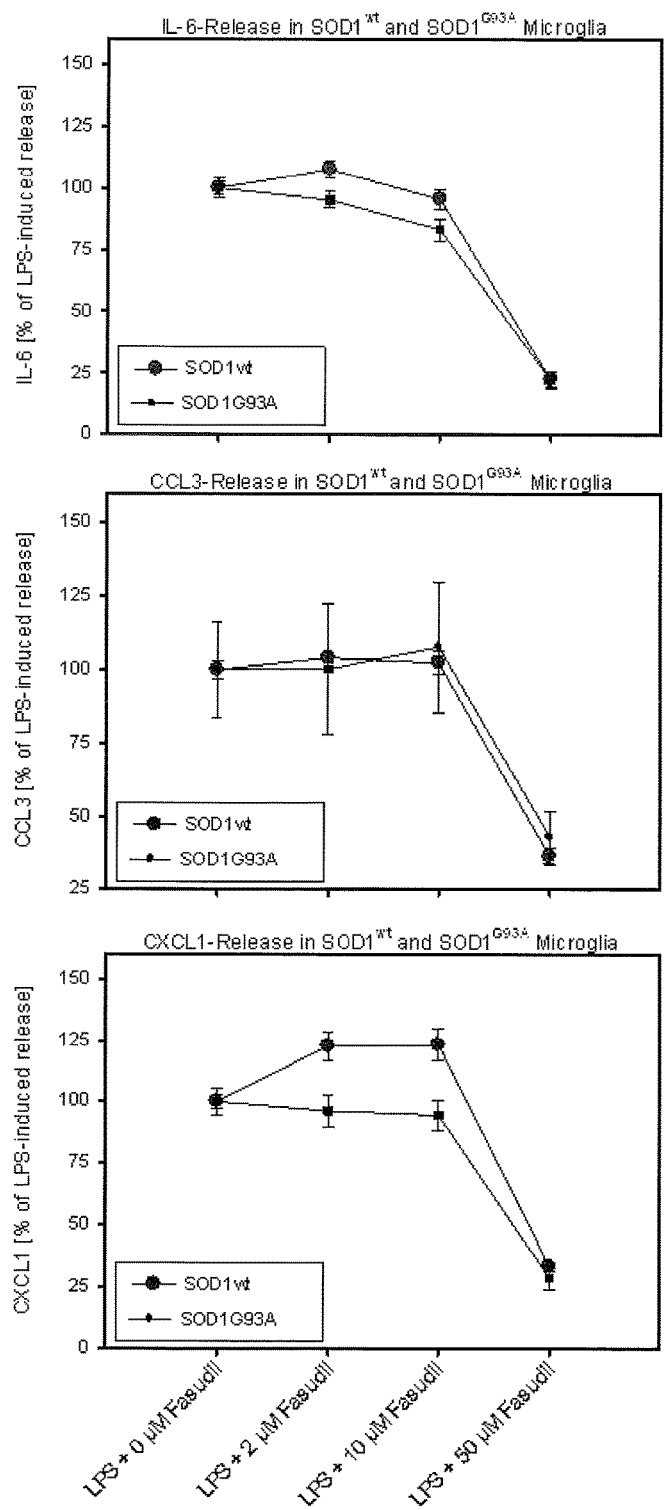

Primary cultures of newborn SOD1 wild-type control (SOD1 wt) or respective mutant (from advanced clinical SOD1G93A mice) microglia (15,000 cells/well) were incubated in the simultaneous presence of LPS (10 ng/ml) and different Fasudil concentrations (2 µM, 10 µM, 50 µM) for 18 hours, respectively. Cytokine/chemokine release profile was determined in the supernatants. The results are shown in FIG. 22. Data are presented relative to the corresponding value of LPS-triggered cytokine/chemokine release within each genotype, respectively (set as 100%). Data are mean±SEM of quadruplicates of 2 independent experiments.

Whereas Fasudil at concentrations of 2 µM and 10 µM was not efficient in significantly reducing the harmful proinflammatory cytokine release (cf. Henkel et al. 2009) of both, SOD1 wt and SOD1G93A microglia, the dose of 50 µM Fasudil markedly reduced the release of TNFα, IL-6, CCL3, RANTES and CXCL1 in both genotypes. These factors are generally supposed in mediating an harmful inflammatory response. In contrast, values for CCL2 were slightly increased (+8.9%)/unaffected at this dose.

In summary, and without being bound by theory, the prolonged survival and disease duration in fasudil treated SOD G93A mice as described in Example 1 may possibly be explained by an increased infiltration of neuroprotective M2 microglial cells.

LIST OF REFERENCES

EP 1110553
U.S. Pat. No. 5,942,505
U.S. Pat. No. 4,678,783
WO 2009/155777 A1
WO 2005/117896 A1
Bermel, C., L. Tonges, et al. (2009). "Combined inhibition of Cdk5 and ROCK additively increase cell survival, but not the regenerative response in regenerating retinal ganglion cells." *Mol Cell Neurosci* 42(4): 427-437.

Bowerman, M., A. Beauvais, et al. (2010). "Rho-kinase inactivation prolongs survival of an intermediate SMA mouse model." *Hum Mol Genet* 19(8): 1468-1478.

Cedarbaum, J. M., Stambler N, et al. (1999). "The ALSFRS-R: a revised ALS functional rating scale that incorporates assessments of respiratory function. BDNF ALS Study Group (Phase III)." *J Neurol Sci.,* 169(1-2): 13-21.

de Carvalho et al. (2008). "Electrodiagnostic criteria for diagnostic of ALS." *Clin Neurophysiol* 119: 497-503.

de Carvalho, M., Swash, M. (2011). "Amyotrophic lateral sclerosis: an update." *Curr Opin Neurol* 24; 497-503.

Davies, S. P., H. Reddy, et al. (2000). "Specificity and mechanism of action of some commonly used protein kinase inhibitors." *Biochem J* 351(Pt 1): 95-105.

Graeber, M. B. (2010) "Changing Face of Microglia." *Science* 330(6005): 783-788.

Gurney, M. E., H. Pu, et al. (1994). "Motor neuron degeneration in mice that express a human Cu, Zn superoxide dismutase mutation." *Science* 264(5166): 1722-1775.

Henkel, J. S., D. R. Beers, et al. (2009). "Microglia in ALS: the Good, the Bad, and the Resting." *Journal of Neuroimmune Pharmacology: the Official Journal of the Society on Neurolmmune Pharmacology* 4(4): 389-398.

Kong, J. and Z. Xu (1998). "Massive mitochondrial degeneration in motor neurons triggers the onset of amyotrophic lateral sclerosis in mice expressing a mutant SOD1." *J Neurosci* 18(9): 3241-3250.

Li, M., Y. Huang, et al. (2009). "Y-27632 improves rotarod performance and reduces huntingtin levels in R6/2 mice." *Neurobiol Dis* 36(3): 413-420.

Lingor, P., N. Teusch, et al. (2007). "Inhibition of Rho kinase (ROCK) increases neurite outgrowth on chondroitin sulphate proteoglycan in vitro and axonal regeneration in the adult optic nerve in vivo." *J Neurochem* 103(1): 181-189.

Lingor, P., L. Tonges, et al. (2008). "ROCK inhibition and CNTF interact on intrinsic signaling pathways and differentially regulate survival and regeneration in retinal ganglion cells." *Brain* 131(Pt 1): 250-263.

Meyer zu Horste, G., T. Prukop, et al. (2007). "Antiprogesterone therapy uncouples axonal loss from demyelination in a transgenic rat model of CMT1A neuropathy." *Ann Neurol* 61(1): 61-72.

Pitzer, C., C. Kruger, et al. (2008). "Granulocyte-colony stimulating factor improves outcome in a mouse model of amyotrophic lateral sclerosis." *Brain* 131(Pt 12): 3335-3347.

Planchamp, V., C., Bermel, et al. (2008). "BAG1 promotes axonal outgrowth and regeneration in vivo via Raf-1 and reduction of ROCK activity." *Brain* 131(Pt 10): 2606-2619.

Regen, T., Van Rossum, D., Scheffel, J., Kastriti, M. E., Revelo, N. H., Prinz, M., Brück, W., and Hanisch, U. K. (2011) "CD14 and TRIF Govern Distinct Responsiveness and Responses in Mouse Microglial TLR4 Challenges by Structural Variants of LPS." *Brain, Behavior, and Immunity* 25(5): 957-970.

The invention claimed is:

1. A method of treating a subject suffering or prone to suffer from familial ALS, wherein the method comprises administering a pharmaceutical composition, comprising or consisting of fasudil (1-(5-isoquinolinesulfonyl)homopiperazine), or a fasudil derivative selected from hydroxy-fasudil (1-(1-hydroxy-5-isoquinolinesulfonyl)homopiperazine) and dimethyl-fasudil ((S)-(+)-2-Methyl-1-[(4-methyl-5-isoquinolinyl)sulfonyl]-hexahydro-1H-1,4-diazepine), or a pharmaceutically acceptable salt thereof, to the subject, wherein the familial ALS is early stage ALS as diagnosable by the Awaji-shima diagnostic criteria, and wherein the administration of said composition is started presymptomatically.

2. The method of claim 1, wherein the subject is a female.

3. The method of claim 1, wherein the pharmaceutical composition is to be administered orally.

4. The method of claim 1, wherein the pharmaceutical composition comprises or consists of fasudil.

5. The method of claim 4, wherein the fasudil is to be administered to the subject in a dosage of 1-12 mg/kg body weight per day.

6. The method of claim 1, wherein the pharmaceutical composition comprises or consists of a fasudil derivative selected from hydroxy-fasudil and dimethyl-fasudil.

7. The method of claim 6, wherein the fasudil derivative is to be administered to the subject in a dosage of 10-1200 ng/kg body weight per day.

8. The method of claim 1, wherein the fasudil, fasudil derivative, or a pharmaceutically acceptable salt thereof is formulated as a formulation with sustained release or prolonged release.

9. A method of improving motor coordination in a subject suffering or prone to suffer from familial ALS, wherein the method comprises administering a pharmaceutical composition, comprising or consisting of fasudil, or a fasudil derivative selected from hydroxy-fasudil and dimethyl-fasudil, or a pharmaceutically acceptable salt thereof, to the subject, wherein the familial ALS is early stage ALS as diagnosable by the Awaji-shima diagnostic criteria, and wherein the administration of said composition is started presymptomatically.

10. The method of claim 9, wherein the subject is a female.

11. The method of claim 9, wherein the pharmaceutical composition is to be administered orally.

12. The method of claim 9, wherein the pharmaceutical composition comprises or consists of fasudil.

13. The method of claim 12, wherein the fasudil is to be administered to the subject in a dosage of 1-12 mg/kg body weight per day.

14. The method of claim 9, wherein the pharmaceutical composition comprises or consists of a fasudil derivative selected from hydroxy-fasudil and dimethyl-fasudil.

15. The method of claim 14, wherein the fasudil derivative is to be administered to the subject in a dosage of 10-1200 ng/kg body weight per day.

16. The method of claim 9, wherein the fasudil, fasudil derivative, or a pharmaceutically acceptable salt thereof is formulated as a formulation with sustained release or prolonged release.

* * * * *